United States Patent [19]
Luter

[11] Patent Number: 5,951,557
[45] Date of Patent: Sep. 14, 1999

[54] BONE PLATE

[76] Inventor: Dennis W. Luter, 2705 Bloom Meadow, Jonesboro, Ark. 72404

[21] Appl. No.: 09/001,131

[22] Filed: Dec. 30, 1997

[51] Int. Cl.⁶ ..................................................... A61B 17/80
[52] U.S. Cl. ............................................... 606/69; 606/71
[58] Field of Search ................................ 606/60, 61, 69, 606/70, 71

[56] References Cited

U.S. PATENT DOCUMENTS

| | | | |
|---|---|---|---|
| Re. 31,628 | 7/1984 | Allgower et al. | 606/69 |
| 2,443,363 | 6/1948 | Townsend et al. | 606/71 |
| 3,488,779 | 1/1970 | Christensen | 623/18 |
| 3,659,595 | 5/1972 | Haboush | 606/71 |
| 3,716,050 | 2/1973 | Johnston | 606/69 |
| 3,779,240 | 12/1973 | Kondo | 606/69 |
| 4,297,993 | 11/1981 | Harle | 606/70 |
| 4,338,926 | 7/1982 | Kummer et al. | 606/70 |
| 4,493,317 | 1/1985 | Klaue | 606/69 |
| 4,573,458 | 3/1986 | Lower | 606/69 |
| 4,705,031 | 11/1987 | Wolter | 606/69 |
| 4,838,252 | 6/1989 | Klaue | 606/69 |
| 4,969,886 | 11/1990 | Cziffer et al. | 606/59 |
| 5,002,544 | 3/1991 | Klaue et al. | 606/69 |
| 5,041,114 | 8/1991 | Chapman et al. | 606/62 |
| 5,151,103 | 9/1992 | Tepic et al. | 606/69 |
| 5,326,367 | 7/1994 | Robioneck | 623/22 |
| 5,344,422 | 9/1994 | Frigg | 606/61 |
| 5,372,598 | 12/1994 | Luhr et al. | 606/69 |
| 5,380,327 | 1/1995 | Eggers et al. | 606/69 |
| 5,462,547 | 10/1995 | Weigum | 606/65 |
| 5,484,439 | 1/1996 | Olson et al. | 606/65 |
| 5,501,684 | 3/1996 | Schlapfer et al. | 606/73 |
| 5,549,680 | 8/1996 | Gordon | 623/18 |
| 5,569,250 | 10/1996 | Sarver et al. | 606/69 |
| 5,601,553 | 2/1997 | Trebing et al. | 606/61 |
| 5,607,430 | 3/1997 | Bailey | 606/74 |

FOREIGN PATENT DOCUMENTS

| | | |
|---|---|---|
| 4 201 043 | 7/1993 | Germany . |
| 1648423 | 5/1991 | U.S.S.R. . |

Primary Examiner—Michael Buiz
Assistant Examiner—David O. Reip
Attorney, Agent, or Firm—Garrison Morris & Haight

[57] ABSTRACT

A bone plate for use in stabilizing a fractured bone is provided having first and second end portions longitudinally spaced from one another and an intermediate portion extending between and interconnecting the end portions. The end portions and intermediate portion combine to define an upper surface, a lower surface for application to a bone, and an edge extending between the upper and lower surfaces. The plate includes at least one interior hole formed in the intermediate portion for receiving a fastener such as a bone screw to attach the plate to the fractured bone. A plurality of apertures are formed in the plate, with each of the end portions including at least one of the apertures which extend through the plate from the upper surface to the lower surface for receiving a bone screw. Each aperture also extends to and through the edge of the plate whereby each aperture may be temporarily positioned around an external fixation rod temporarily secured to the bone, which facilitates positioning the bone plate. Fasteners may be inserted through the apertures to further secure the plate after the rods have been removed. The plate may have a variety of shapes including rectangular, L-shape, Y-shape and others. Depending upon the size of the apertures formed in the end portions, washers may be used in conjunction with the apertures in the end portions to receive bone screws.

43 Claims, 11 Drawing Sheets

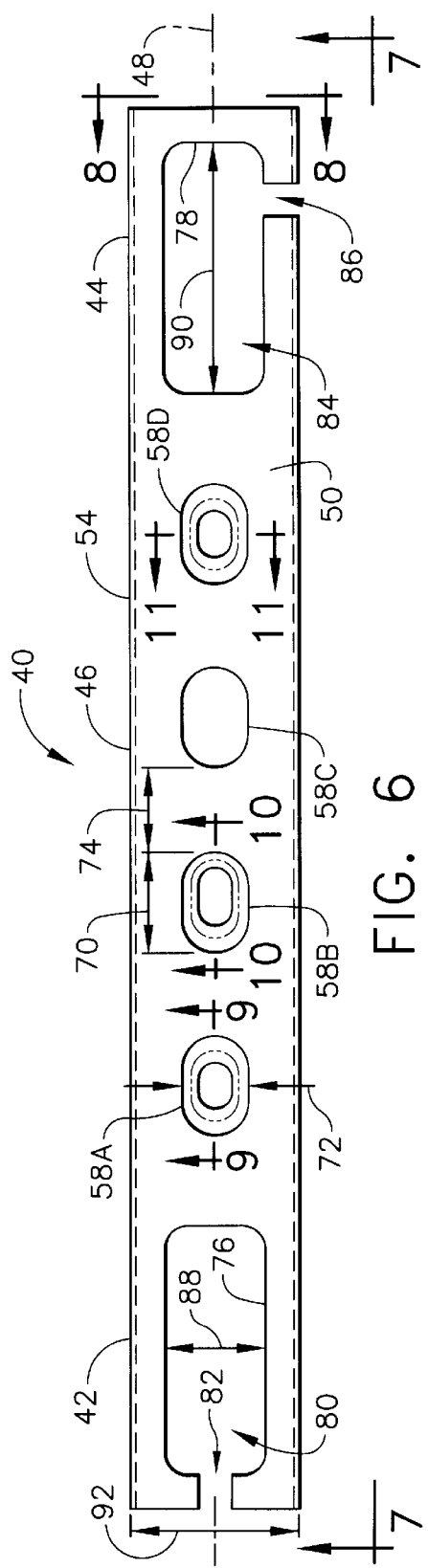

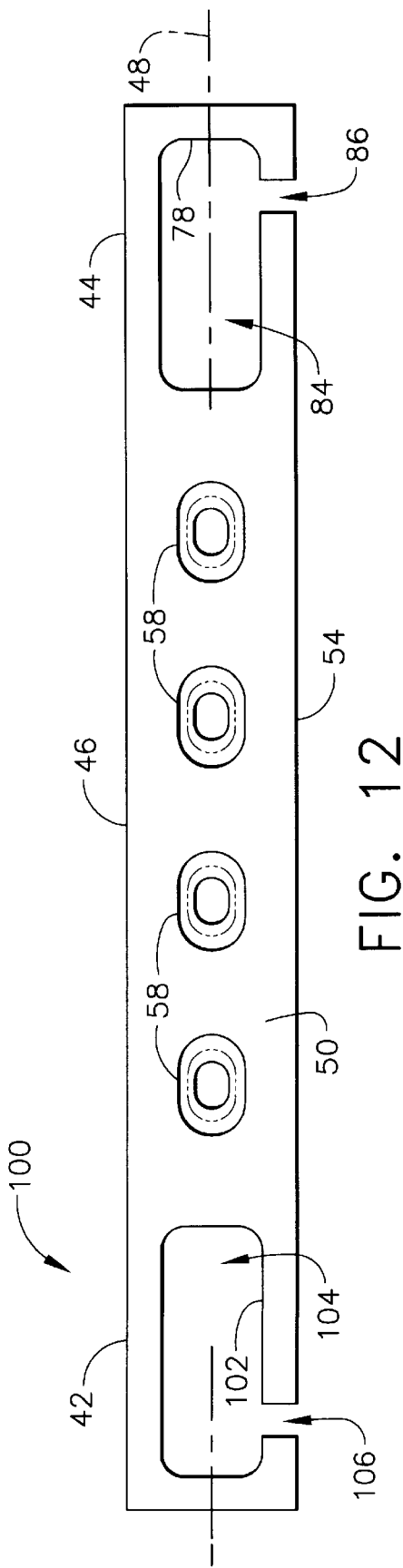
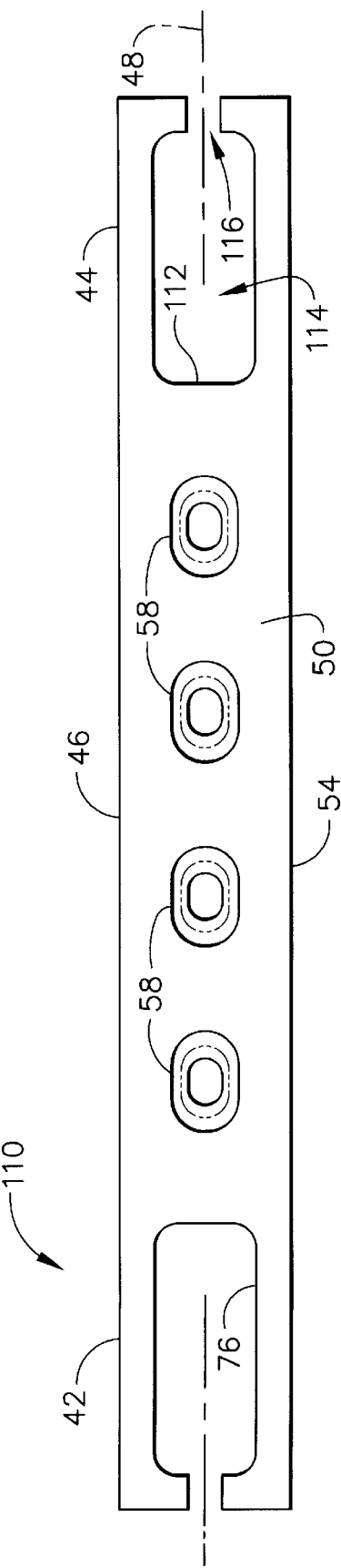

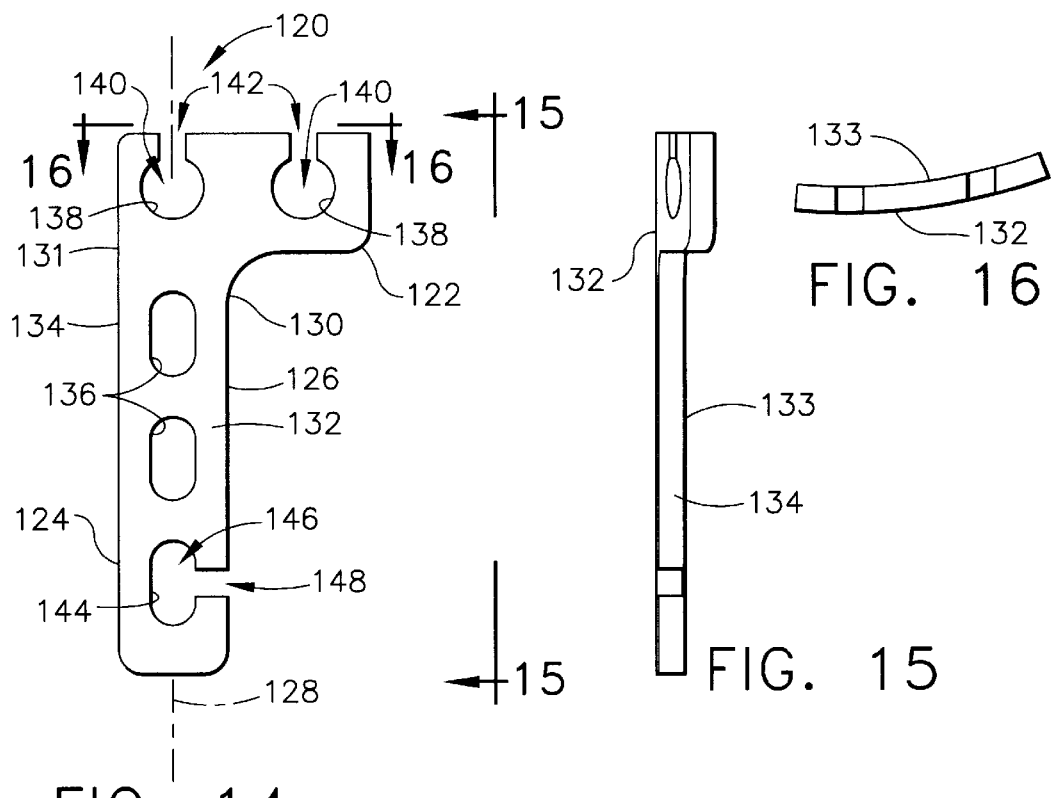
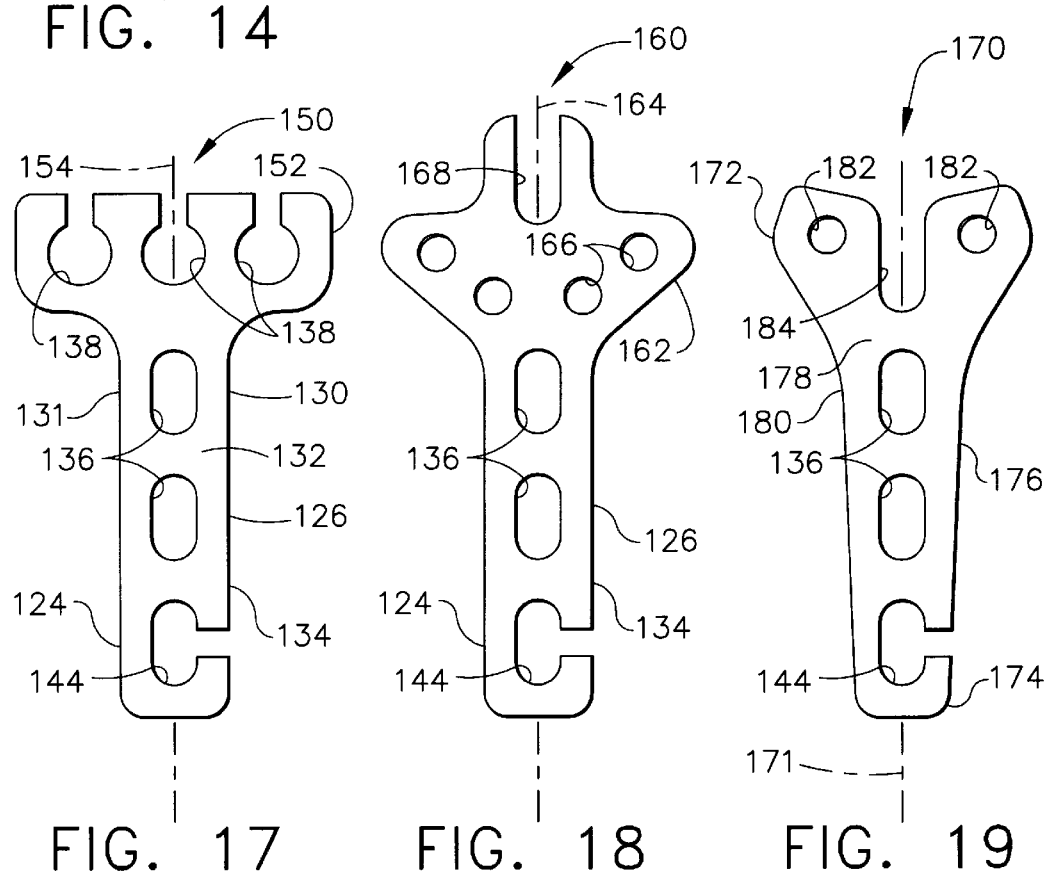

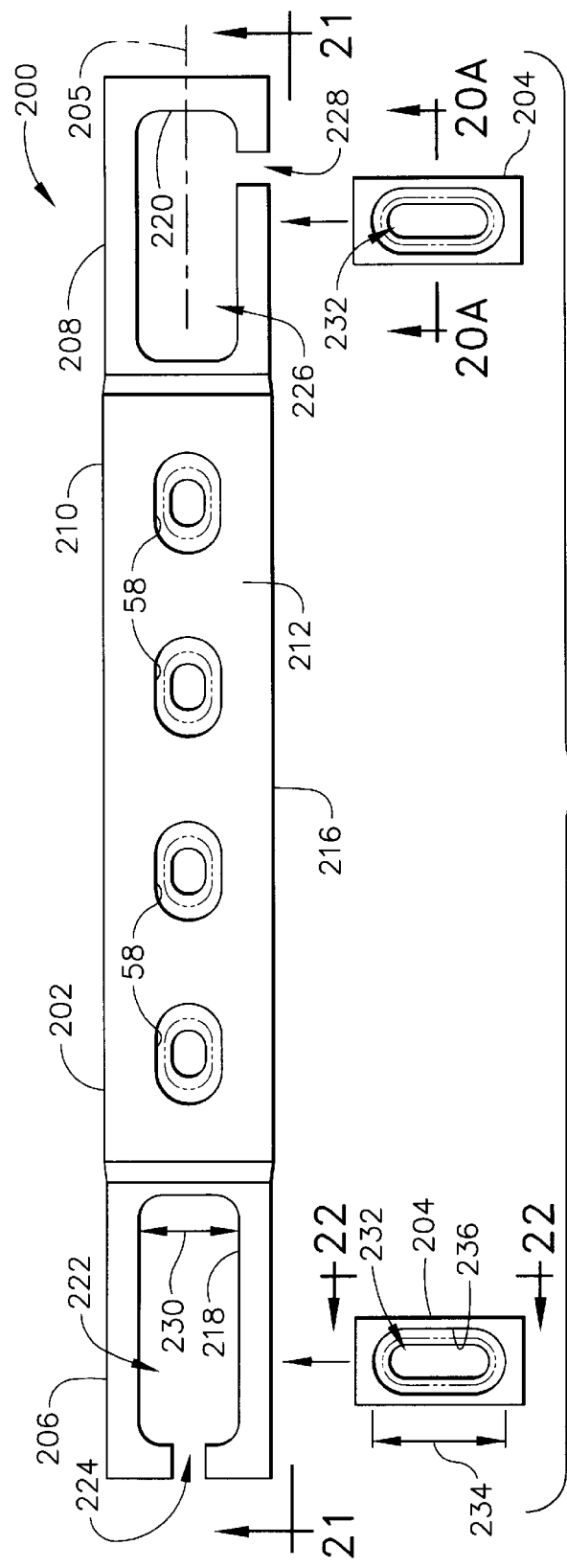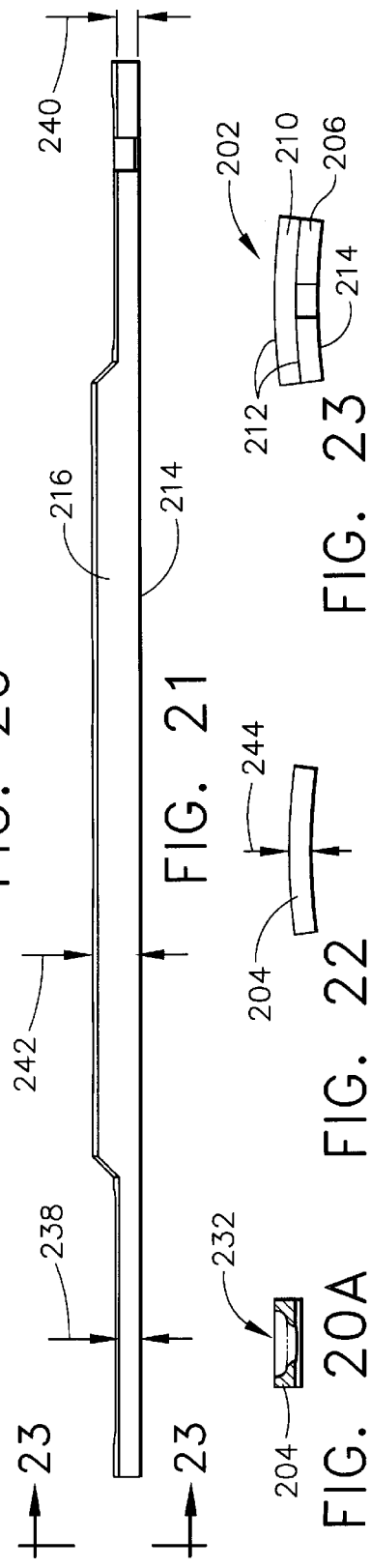

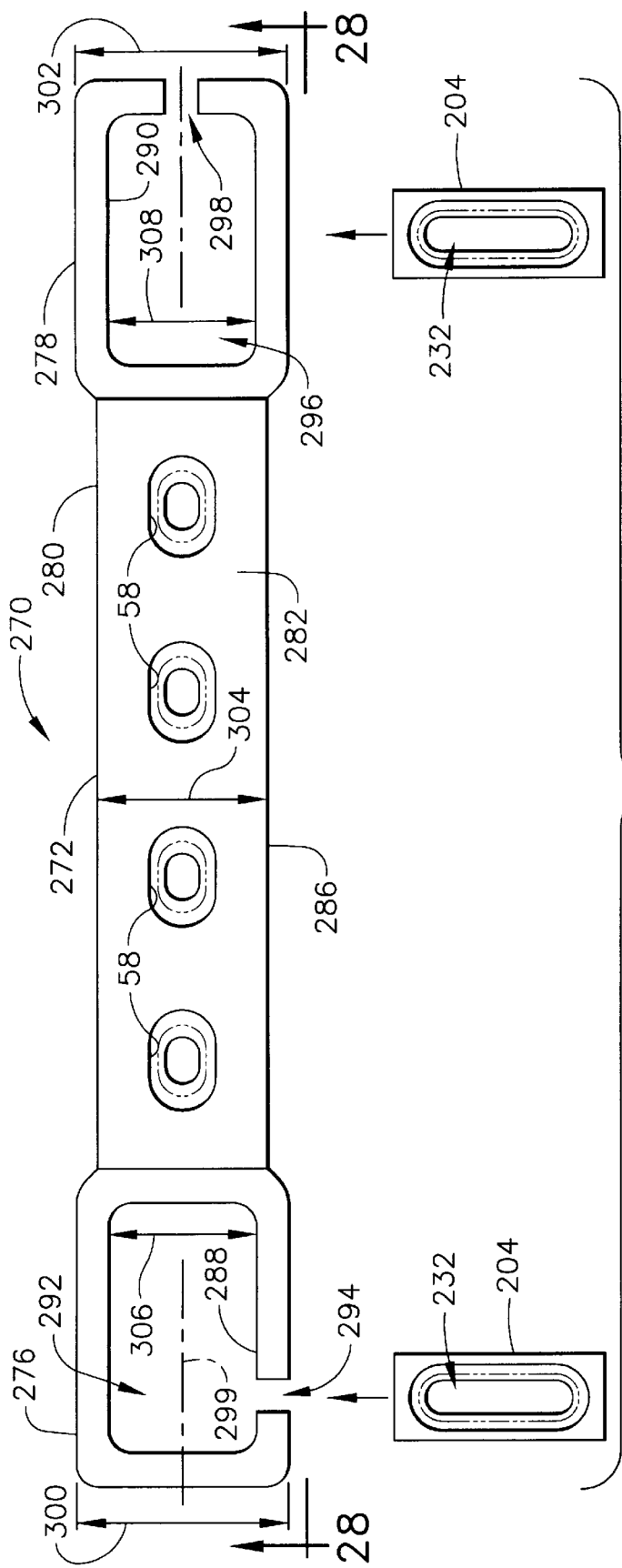
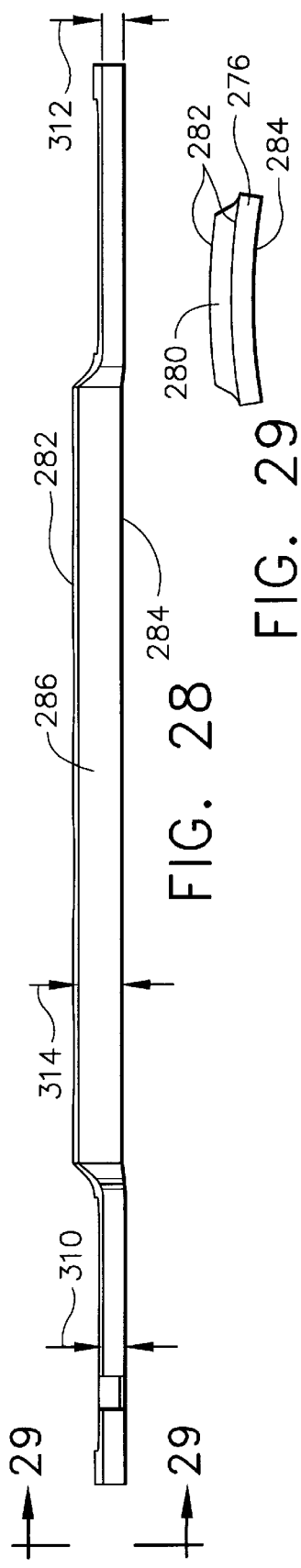
FIG. 27
FIG. 28
FIG. 29

BONE PLATE

BACKGROUND OF THE INVENTION

1.0 Field of the Invention

The present invention relates generally to orthopaedic implants and, more particularly, to bone plates and bone plate assemblies which may be implanted in various parts of the human body to stabilize bone fractures.

2.0 Related Art

Orthopaedic surgeons frequently encounter bone fractures which require surgical stabilization with implants including metal bone plates having a variety of shapes. Difficulties in the repair of these fractures include insufficient assistants in the operating theater and fractures that are difficult to reduce (i.e., returning the fractured bone segments to their proper positions) and hold. Conventional bone plates may be generally classified as either "compression plates" or "one-third semi-tubular plates." Both types of plates are available in a variety of shapes, for use in stabilizing various bones, and typically include a plurality of interior holes (i.e., spaced apart from the edge of the plate and surrounded by metal) which accept bone screws to secure the plates to the fractured bone segments. Furthermore, both types of bone plates may be somewhat curved, as seen in an end view, to accommodate the cross-sectional shape of the particular bone. Compression plates are relatively thicker and the included interior holes are typically "compression holes" having either one or two ramps which extend longitudinally toward the center of the hole from the outer to the inner surface of the plate. The compression holes cause the bone plate to move longitudinally relative to the bone screws used to secure the plate, as the screws are tightened. The one-third semi-tubular plates are relatively thinner and typically include straight-through holes without the foregoing longitudinally extending ramps.

Both compression plates and one-third semi-tubular plates have been widely and successfully used to stabilize bone fractures. However, the implantation of either type of plate may be problematic for the surgeon in certain instances as illustrated in the subsequent discussion regarding a typical procedure for implanting conventional bone plates.

The bone fracture is approached through a standard incision. Soft tissue such as periosteum, muscle, arteries and veins are partially stripped from the bone to allow visualization of the area and to allow temporary placement of bone clamps and the implantation of the bone plate or plates. The surgeon commonly faces situations in which he or she struggles to achieve alignment of the fractured bones with the use of bone clamps, only to have to remove the same clamps securing the reduction in order to position and attach the bone plate. A bone clamp may be used to reduce the fracture by applying it directly around the fracture, if the fracture pattern is amenable, i.e. such as an oblique fracture. The fracture may also be reduced by placing clamps above and below the fracture site and applying traction against each end until the bone segments are realigned. Either method requires stripping of soft tissue off of bone and additional soft tissue trauma, and potential devitalization of bone.

After the fracture is reduced, the bone segments must then be held in place to allow removal of the clamps to permit placement of the bone plate. In some instances, the fracture may be secured by placing a bone screw across the fracture site, but this is only feasible if the fracture is oblique and is not excessively comminuted (i.e., broken into more than two pieces). However, the screw head may be disposed in an area that interferes with placement of the bone plate, creating additional difficulties. Commonly, the surgeon must try to add and subtract clamps as he or she implants the bone plate. This procedure may be compounded by the bending and contouring of the plate that is usually necessary, requiring repeated engagement and disengagement of the clamps. Not only is this procedure difficult, frustrating and time consuming, it may result in a loss of fracture alignment and creates additional soft tissue stripping and trauma. Once the bone plate is finally properly positioned, it is secured with bone screws, x-rays are performed, and the wound is closed.

In view of the foregoing disadvantages associated with the surgical implantation of conventional bone plates, a need exists for an improved bone plate which reduces operating room time, open wound time, anesthesia time and minimizes the risk to the patient.

SUMMARY

In one aspect of the present invention, the foregoing need is fulfilled by providing a bone plate for use in stabilizing a bone having a fracture site, with the bone being reduced by a pair of external fixation rods secured to the bone on either side of the fracture site. The bone plate which comprises a longitudinally extending axis, first and second end portions longitudinally spaced from one another, and an intermediate portion extending between and interconnecting the first and second end portions. The two end portions and the intermediate portion combine to define an upper surface, a lower surface for application to a bone, and an edge extending between the upper and lower surfaces comprising a perimeter of the bone plate. In each embodiment, the bone plate includes at least one interior hole, and preferably a plurality of interior holes, for receiving bone screws to secure the bone plate to a fractured bone. Each of the interior holes are spaced apart from the edge of the bone plate.

Each embodiment further includes a plurality of apertures formed in the plate, with each aperture extending through the plate from the upper surface to the lower surface for receiving a bone screw. Each of the apertures extends to and through the edge of the plate, whereby each of the apertures may be temporarily positioned around one of the external fixation rods, in a position proximate the fractured bone, by moving the bone plate relative to the rod. This facilitates placement of the bone plate on the bone. Each aperture is effective for receiving a bone screw after the corresponding external fixation rod is removed from the bone. In each embodiment, both the first and second end portions include at least one of the apertures. In one preferred embodiment, at least one of the apertures formed in the plate extends transversely to and through the edge of the plate.

In another preferred embodiment, both the first and second end portions of the plate include a single one of the apertures, with the aperture formed in the first end portion extending longitudinally to and through the edge of the plate and the aperture formed in the second portion extending transversely to and through the edge of the plate. In another preferred embodiment, the single aperture formed in the first end portion, as well as the single aperture formed in the second end portion, extends transversely to and through the edge of the plate. In yet another preferred embodiment, the single aperture formed in the first end portion and the single aperture formed in the second end portion extend longitudinally to and through the edge of the plate. In other preferred embodiments, one of the end portions may include at least two of the apertures, each extending longitudinally to and through the edge of the plate.

The apertures in the end portions of the plate may have various shapes. For instance, in several embodiments, each aperture has an interior portion having a generally rectangular shape and a slot communicating with the interior portion and extending to and through the edge of the plate. The slot may extend longitudinally or transversely to and through the edge of the plate. In other embodiments, the end portion apertures may have a key-hole or generally U-shape.

The bone plate may have a variety of shapes which include a generally rectangular shape, a generally cloverleaf shape and generally Y, L or T shapes. In the embodiments where the plate has a generally cloverleaf or Y-shape, the plate may include a second plurality of interior holes formed in one of the end portions which are effective for receiving bone screws for further securing the plate to the fractured bone.

According to a second aspect of the present invention, the foregoing need is provided by a bone plate assembly having a bone plate and a pair of washers. Each washer is disposed in contacting engagement with the upper surface of the bone plate. The bone plate may comprise any of the previously discussed bone plates of the present invention, having at least one aperture formed in each end portion of the plate and extending to and through the edge of the plate. Each washer has an interior aperture which is aligned with one of the apertures formed in the first and second end portions of the plate. Accordingly, a bone screw may be inserted through the washer and the corresponding aperture in the bone plate, for securing the plate to a fractured bone. The use of the washers permits the end portion apertures of the plate to be larger in size, thereby facilitating placement of the bone plate around a pair of external fixation rods used to reduce the bone.

Each of the end portions of the plate may have a reduced thickness, relative to the intermediate portion extending between the end portions, so that the overall thickness of the assembly with washers installed is not excessive. This feature minimizes the chance that the bone plate assembly will create a bulge in the skin overlying the fractured bone, after the assembly has been secured to the bone.

In other embodiments, the first and second end portions of the plate may have an enlarged width, relative to the width of the intermediate portion of the plate, thereby permitting the end portion apertures to have an enlarged width which facilitates positioning of the bone plate around the pair of external fixation rods.

The bone plate assembly may further include a means for laterally retaining the washers on the bone plate. This means for laterally retaining the washers may comprise a pair of flanges which are attached to and extend downwardly from the remaining portion of the washer and are disposed adjacent the edge of the plate.

BRIEF DESCRIPTION OF THE DRAWINGS

These and other features, aspects and advantages of the present invention will become more apparent from the subsequent detailed description when considered in conjunction with the accompanying drawings wherein:

FIG. 6 is a plan view illustrating a bone plate according to a first embodiment of the present invention;

FIG. 7 is a side elevation view taken along line 7—7 in FIG. 6;

FIG. 8 is an end elevation view taken along line 8—8 in FIG. 6;

FIG. 9 is a cross-sectional view taken along line 9—9 in FIG. 6;

FIG. 10 is a cross-sectional view taken along line 10—10 in FIG. 6;

FIG. 11 is a cross-sectional view taken along line 11—11 in FIG. 6;

FIG. 12 is a plan view illustrating a bone plate according to a second embodiment of the present invention;

FIG. 13 is a plan view illustrating a bone plate according to a third embodiment of the present invention;

FIG. 14 is a plan view illustrating a bone plate according to a fourth embodiment of the present invention;

FIG. 15 is a side elevation view taken along line 15—15 in FIG. 14;

FIG. 16 is an end elevation view taken along line 16—16 in FIG. 14;

FIG. 17 is a plan view illustrating a bone plate according to a fifth embodiment of the present invention;

FIG. 18 is a plan view illustrating a bone plate according to a sixth embodiment of the present invention;

FIG. 19 is a plan view illustrating a bone plate according to a seventh embodiment of the present invention;

FIG. 20 is an exploded assembly plan view of a bone plate assembly according to a first embodiment of the present invention;

FIG. 20A is a cross-sectional view, taken along line 20A—20A in FIG. 20, of one of the washers shown in FIG. 20;

FIG. 21 is a side elevation view, taken along line 21—21 in FIG. 20, of the bone plate shown in FIG. 20;

FIG. 22 is a side elevation view, taken along line 22—22 in FIG. 20, of one of the washers shown in FIG. 20;

FIG. 23 is an end elevation view taken along line 23—23 in FIG. 21;

FIG. 27 is an exploded assembly plan view illustrating a bone plate assembly according to a third embodiment of the present invention;

FIG. 28 is a side elevation view, taken along line 28—28 in FIG. 27, of the bone plate shown in FIG. 27;

FIG. 29 is an end elevation view taken along line 29—29 in FIG. 28;

DETAILED DESCRIPTION

Figure 1:
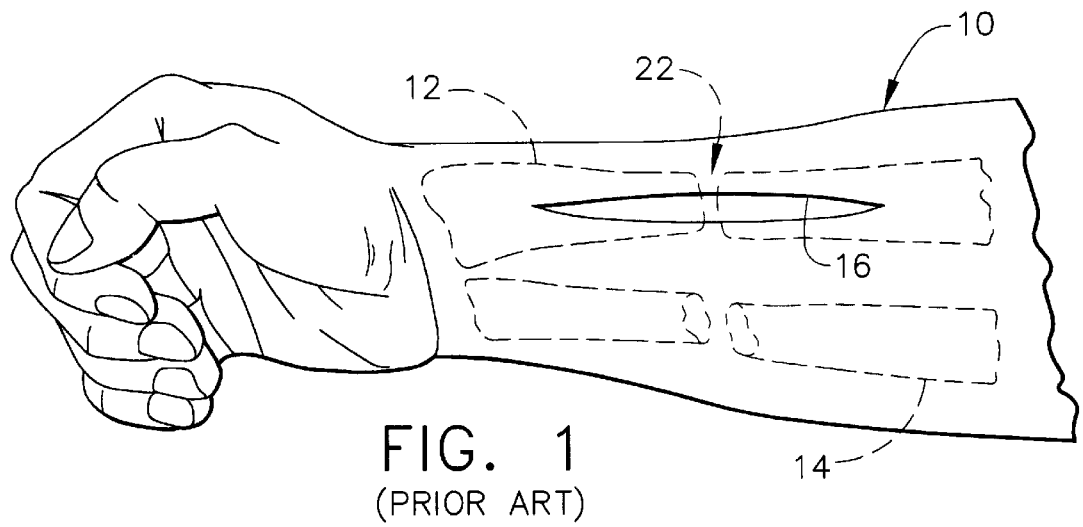
FIG. 1 is a side elevation view illustrating a portion of the right arm of a person having fractured radius and ulna bones.

Referring now to the drawings, the problems which may be encountered during insertion or implantation of conventional bone plates discussed previously in the Background of this application, may be further understood with reference to FIGS. 1–5. FIG. 1 is a side elevation view of the right arm 10 of a human which includes a pair of bones known as the radius 12 and ulna 14. As shown in FIG. 1, both the radius 12 and ulna 14 are fractured. FIG. 1 further illustrates a surgical incision 16 in the area of one of the fracture sites. The fractures in the radius 12 and ulna 14 are the type which commonly require the use of bone plates or other implants to stabilize the fracture. Soft tissue such as periosteum, muscle, arteries and veins are partially stripped from each of the bones 12 and 14 to allow visualization of the respective fracture sites and to allow temporary placement of bone clamps and the implantation of the required bone plates.

Figure 2:
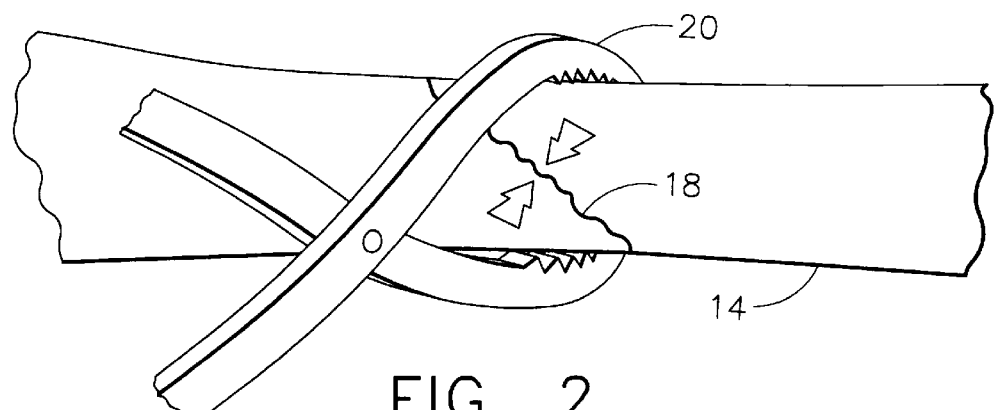
FIG. 2 is a view illustrating a prior art bone clamp which is clamped across the oblique fracture existing in the right arm ulna shown in FIG. 1.
Figure 3:
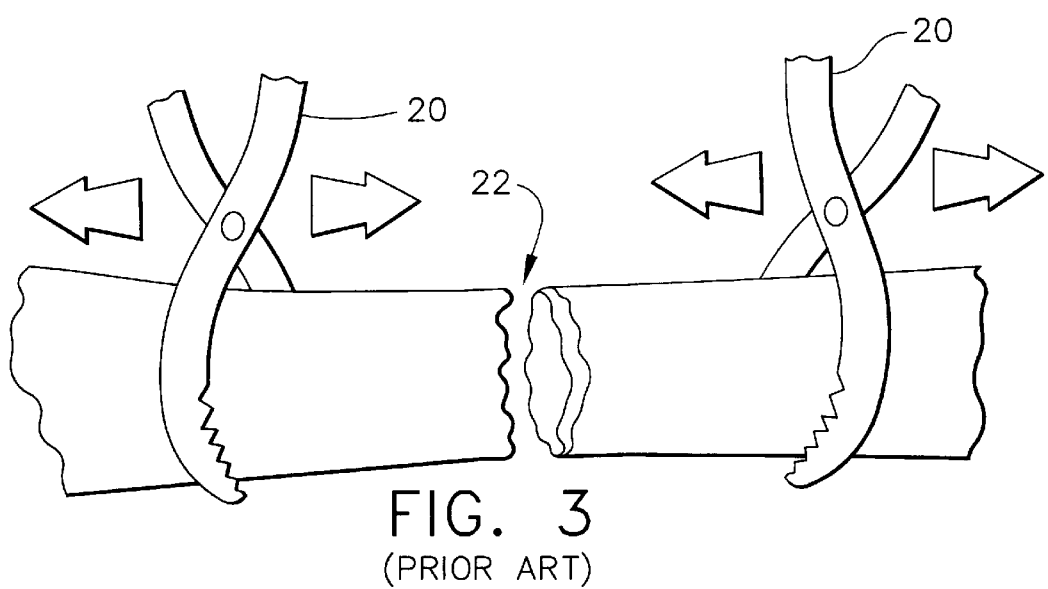
FIG. 3 is a view illustrating a pair of prior art bone clamps which are used to reduce the transverse fracture in the right arm radius shown in FIG. 1.

In general, the orthopaedic surgeon responsible for repairing fractured bones commonly faces the situation in which he or she struggles to achieve alignment of the fractured bones with the use of bone clamps, only to have to remove the same clamps securing the reduction in order to position and attach the bone plate. As shown in FIGS. 1 and 2 the ulna 14 has sustained an oblique fracture 18. With this type of fracture, a single bone clamp 20 may be used to reduce the fracture, for instance by placing it directly around the fracture 18 as shown in FIG. 2. This procedure is not suitable for reducing substantially transverse fractures, such as the fracture indicated generally at 22 in the radius 12, as shown in FIGS. 1 and 3. In this instance, fracture 22 is reduced by placing a first bone clamp 20 above fracture 22 and a second bone clamp 20 below fracture 22. The foregoing methods of reducing the ulna 14 and radius 12, both require the stripping of soft tissue off of the corresponding bones and additional soft tissue trauma, as well as potential devitalization of the ulna 14 and radius 12. It is noted that the foregoing stripping of soft tissue is required substantially around the entire circumferential extent of each bone in the areas that the bone clamps are applied. After the fracture is reduced, the bone segments must be held in place to allow removal of the bone clamps 20 to permit placement of the bone plate.

Figure 4:
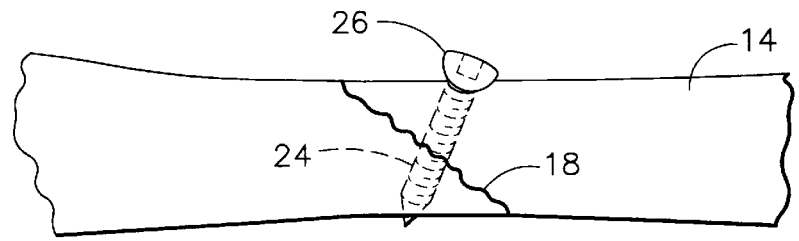
FIG. 4 is a view illustrating the use of a prior art bone screw to secure the oblique fracture in the ulna shown in FIG. 1.

As shown in FIG. 4, the fracture 18 of the ulna 14 is secured by threading a bone screw 24 into the ulna 14 so that screw 14 extends across the fracture 18. This method may be used since the fracture 18 is oblique and is not excessively comminuted. However, with other types of fractures, fasteners such as bone screw 24 may not be acceptable for securing the fracture site. Furthermore, bone screw 24 includes a head 26 which extends above the surface of the ulna 14 and may interfere with the required placement of the bone plate, creating additional difficulties.

Figure 5:
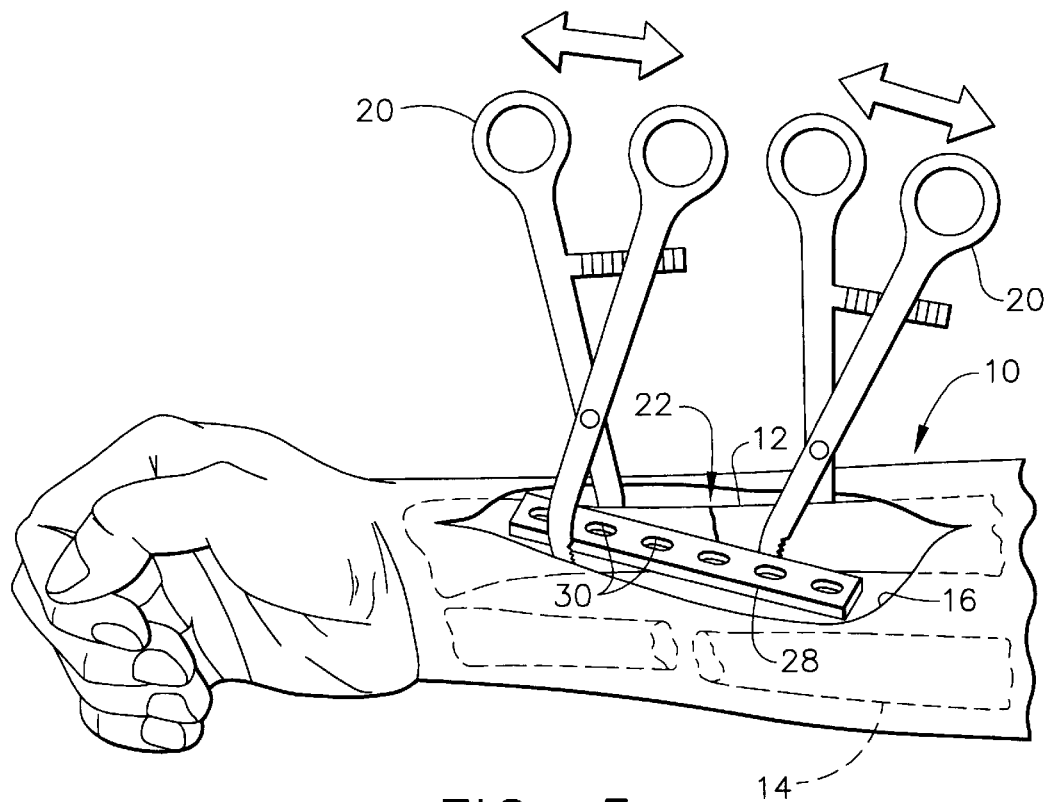
FIG. 5 is a side elevation view similar to FIG. 1, which also illustrates a pair of prior art bone clamps which are clamped around the fractured radius and a prior art bone plate which is being implanted to stabilize the fractured radius.

FIG. 5 illustrates the fractured radius 12 which is temporarily secured by a pair of bone clamps 20. A conventional bone plate 28 is shown in the process of being positioned by the orthopaedic surgeon (not shown) and in instances such as this, the surgeon commonly must try to add and subtract clamps, such as bone clamps 20 as he or she positions a bone plate such as bone plate 28. As shown in FIG. 5, at least one of the bone clamps 20 prevents proper positioning of bone plate 28. This procedure may be compounded by the bending and contouring of plate 28 that is usually necessary, requiring repeated engagement and disengagement of the bone clamps 20. Not only is this procedure difficult, frustrating and time consuming, it may result in a loss of alignment of fracture 22 and creates additional soft tissue stripping and trauma due to the multiple placements of bone clamps 20. As shown in FIG. 5, bone plate 28 includes a plurality of spaced apart interior holes 30 which are surrounded by material and do not extend to the perimeter of plate 28. Once bone plate 28 is properly positioned, it is secured with bone screws (not shown) which are inserted through the interior holes 30. The interior holes 30 may comprise either straight-through holes or alternatively, may comprise compression holes having one or two ramps which causes the plate 28 to be translated longitudinally relative to the bone as the bone screws are fastened to the bone. After the bone plate 28 has been secured, x-rays are performed and incision 16 is closed.

The subsequently described bone plates and bone plate assemblies (which include a bone plate and a pair of washers) of the present invention may be advantageously used to overcome the foregoing problems associated with known bone plates. Each bone plate of the present invention has at least one aperture formed in each end portion of the bone plate, with the end portion apertures extending to and through the edge of the bone plate. Since the end portion apertures extend through the edge of the bone plate, the bone plate may be advantageously used in conjunction with a pair of external fixation rods temporarily secured to a fractured bone, on either side of the fracture site and interconnected by an external fixation frame attached to an upper end of each rod, for the purpose of reducing the fractured bone. More particularly, the end portion apertures in each of the bone plates of the present invention permit the bone plate to be moved relative to both of the external fixation rods so that each of the end portion apertures is positioned around one of the rods at a position proximate the bone. This facilitates placement of the bone plate onto the bone which is then secured to the bone by conventional fasteners such as bone screws which are inserted through a plurality of interior holes in the bone plate. The positioning of the end portion apertures around the rods also permits the use of the same drill holes which receive the rods, for further securing the plate to the bone by inserting bones screws through the aperture and into these holes after the rods have been removed. This completes the attachment of the bone plate to the bone and the stabilization of the fractures. The ability to place the plate on the bone with one of the end portion apertures positioned around each one of the external fixation rods minimizes or eliminates the need to use conventional bone clamps, in most circumstances, to reduce the bone fracture and therefore avoids the bone clamp/bone plate interference problem typically encountered with the implantation of conventional bone plates. This feature of the bone plate of the present invention also minimizes the need for surgical assistants during fracture stabilization. The foregoing methodology or procedure, is subsequently described in greater detail with reference to FIGS. 30–37.

FIGS. 6–11 illustrate a bone plate 40, according to a first embodiment of the present invention. Bone plate 40 includes a first end portion 42 and a second end portion 44 longitudinally spaced from end portion 42. An intermediate portion 46 extends between and interconnects the first 42 and second 44 end portions. End portions 42 and 44 and intermediate portion 46 are preferably made as a unitary construction. Bone plate 40 further includes a longitudinally extending centerline axis 48. End portions 42 and 44 and intermediate portion 46 are substantially symmetrically disposed about axis 48.

The first end portion 42, the second end portion 44, and the intermediate portion 46 combine to define an upper surface 50, a lower surface 52 and an edge 54 which comprises a perimeter of bone plate 40. As shown in FIG. 7, bone plate 40 has a thickness 56 extending between the upper 50 and lower 52 surfaces and corresponding to the height of edge 54. As shown in FIG. 8, the lower surface 52 is curved in a direction which extends transversely with respect to the centerline axis 48, to facilitate the application of bone plate 40 to a bone. For ease of manufacture, the upper surface 50 is also preferably curved and has a radius of curvature substantially the same as that of the lower surface 52.

Bone plate 40 further includes a plurality of interior holes 58, designated as 58A–58D in FIG. 6. Holes 58 may comprise compression holes, straight-through holes, or a combination of both, depending upon the particular application and the thickness 56 of bone plate 40. Bone plates may be generally subdivided into compression plates and one-third semi-tubular plates, with compression plates being relatively thicker and having a relatively greater structural rigidity than one-third semi-tubular plates. Furthermore, compression plates typically include one or more compression holes which permit longitudinal displacement of the bone plate as fasteners are inserted through the compression holes to attach the plate to the bone. One-third semi-tubular plates typically do not have sufficient thickness to accommodate the included ramps of compression holes. In the illustrative embodiment, bone plate 40 comprises a compression plate, and includes three compression holes, designated as 58A, 58B and 58D. Additionally, for purposes of illustration, plate 40 has been shown to include one straight-through hole designated as 58C. In an alternate embodiment, each of the interior holes 58 may comprise a compression hole.

It is noted that compression holes of the type generally indicated by holes 58A, 58B and 58D are known in the art. As shown in the longitudinal cross-section illustrated in FIG. 9, interior hole 58A includes a first ramp 60 and a second ramp 62 which extend between the upper surface 50 and the lower surface 52 of plate 40. The incorporation of ramps 60 and 62 permit the bone plate 40 to be translated in a longitudinal direction relative to a bone (not shown in FIGS. 6–11) to which plate 40 is attached, as bone screws (not shown) or other fasteners are inserted through holes 58A and 58C, which also includes ramps 60 and 62. For instance, if the bone screw is positioned to engage ramp 60, the bone plate 40 may be translated in a first longitudinal direction 64 as shown in FIG. 9. Alternately, if the bone screw engages ramp 62, bone plate 40 may be translated in a second longitudinal direction 66. This feature may be used to apply either compression or traction to the fractured bone being stabilized by bone plate 40. As shown in the longitudinal cross-sectional view illustrated in FIG. 10, the interior hole 58B includes ramp 60, but does not include ramp 62. As shown in the transverse cross-sectional view illustrated in FIG. 11, interior hole 58D includes a countersink 68 which accommodates the head of a bone screw (not shown) which may be inserted through hole 58D. The remaining compression holes 58A and 58B also preferably include a countersink 68. In the illustrative embodiment, interior hole 58D includes both of the ramps 60 and 62. In alternate embodiments, each of the interior holes 58 may include either one of the ramps 60 and 62 or both of the ramps 60 and 62.

In the illustrative embodiment, each of the interior holes 58 have a generally oblong shape, although other shapes may be used for interior holes 58. As shown in FIG. 6, each of the interior holes 58 has a longitudinal length 70, having a magnitude of about 6 mm opening onto the upper surface 50, and a transverse width 72 having a magnitude of about 4 mm opening onto the upper surface 50. The longitudinal length and transverse width opening onto the lower surface are somewhat reduced, due to the inclusion of one or both of ramps 60 and 62. The foregoing size of holes 58 may accommodate conventional bone screws. In one embodiment, a spacing 74 between each adjacent pair of holes 58 may be about 5 mm in length. However, in other embodiments the spacing between adjacent holes 58, as well as the particular size of holes 58 may vary from the foregoing, depending upon the overall size of the bone plate 40 and the particular application.

Bone plate 40 includes an aperture 76, formed in the first end portion 42, and an aperture 78 formed in the second end portion 44. Both of the apertures 76 and 78 extend through plate 40 from the upper surface 50 to the lower surface 52 and are sized to receive a bone screw (not shown) or equivalent fastener. Additionally, both of the apertures 76 and 78 extend to and through the edge 54 of plate 40. Therefore, each of the apertures 76 and 78 may be temporarily positioned around an external fixation rod secured to a fractured bone, at a position proximate the bone, by moving the plate 40 relative to the rods, as may be further appreciated with reference to the subsequent discussion associated with FIGS. 30–37. After the external fixation rods have been removed, a bone screw may be inserted through each of the apertures 76 and 78 and into one of the same holes used to secure the rods to the bone.

As shown in FIG. 6, aperture 76 extends longitudinally to and through edge 54, while aperture 78 extends transversely to and through the edge 54 of plate 40. Aperture 76 includes an interior portion 80 and a slot 82 which communicates with the interior portion 80 and extends longitudinally to and through the edge 54. Aperture 78 includes an interior portion 84 and a slot 86 which communicates with interior portion 84 and extends transversely to and through edge 54. Slot 86 is preferably substantially perpendicular to the centerline axis 48. As further shown in FIG. 6, the bone plate 40, the interior portion 80 of aperture 76, and the interior portion 84 of aperture 78 each have a generally rectangular shape as viewed in plan. As subsequently discussed, the principles of the present invention may be applied to a wide variety of bone plates having shapes other than that shown in FIG. 6, and with respect to bone plate 40, apertures 76 and 78 may have shapes other than that shown provided that both apertures 76 and 78 extend to and through the edge 54 of plate 40. For instance, apertures 76 and 78 may alternatively have a generally key-hole shape or a generally U-shape.

Both the interior portion 80 of aperture 76 and the interior portion 84 of aperture 78 have a transverse width 88 and a longitudinal length 90 and the bone plate 40 has a transverse width 92. In the illustrative embodiment, the width 88 of each interior portion 80 and 84 may be about 6 mm, which is consistent with the insertion of a convention bone screw through each of the apertures 76 and 78, and the width 92 of plate 40 which may be about 10 mm in the illustrative embodiment. Further, in the illustrative embodiment, the length 90 of each interior portion 80 and 84 is about 15 mm. It should be understood that the magnitude of width 88 and length 90 may vary from the foregoing values, depending upon the overall size of plate 40, provided that conventional bone attachment hardware such as bone screws may pass through the apertures 76 and 78 with the head of the screw or other fastener being retained by plate 40.

FIG. 12 is plan view illustrating a bone plate 100 according to a second embodiment of the present invention. Bone plate 100 is the same as bone plate 40 with the following exceptions. The aperture 76 of bone plate 40 is replaced by an aperture 102 formed in the end portion 42 of bone plate 100. Aperture 102 extends through the plate 100 from the upper surface 50 to the lower surface (not shown) and extends transversely, to and through the edge 54 of plate 100. Aperture 102 includes an interior portion 104, a slot 106 communicating with interior portion 104 and extending transversely to and through the edge 54. Slot 106 is preferably substantially perpendicular to axis 48. Accordingly, both of the apertures 78 and 102 of bone plate 100 extend transversely, to and through edge 54. Therefore, each of the apertures 78 and 102 may be temporarily positioned around an external fixation rod secured to a fractured bone, at a position proximate the bone, by moving the plate relative to each rod, as may be further appreciated with reference to the subsequent discussion associated with FIGS. 30–37. After the external fixation rods have been removed, a bone screw may be inserted through each of the apertures 78 and 102 and into one of the same holes used to secure the rods to the bone. The embodiment illustrated in FIG. 12 requires a somewhat more precise location of the pair of external fixation rods since both of the slots 86 and 106 extend transversely to and through edge 54, as compared to the use of the bone plate 40 wherein slot 86 extends transversely to and through edge 54 and slot 82 extends longitudinally to and through edge 54.

FIG. 13 is a plan view illustrating a bone plate 110 according to a third embodiment of the present invention. Bone plate 110 is the same as bone plate 40 with the following exceptions. The aperture 78 of bone plate 40 is replaced by an aperture 112 formed in the end portion 42 of bone plate 110. Aperture 112 extends through the plate 110 from the upper surface 50 to the lower surface (not shown) and extends longitudinally to and through the edge 54 of plate 110. Aperture 112 includes an interior portion 114, a slot 116 communicating with the interior portion 114 and extending longitudinally to and through the edge 54. Accordingly, both of the apertures 76 and 112 of bone plate 110 extend longitudinally to and through edge 54. Therefore, each of the apertures 76 and 112 may be temporarily positioned around an external fixation rod secured to a fractured bone, at a position proximate the bone, by moving the plate 110 relative to the rods as may be further appreciated with reference to the subsequent discussion associated with FIGS. 30–37. After the external fixation rods have been removed, a bone screw may be inserted through each of the apertures 76 and 112 and into one of the same holes used to secure the rods to the bone.

Although each of the interior holes 58 in the intermediate portion 46 of both plates 100 and 110 have been illustrated in FIGS. 12 and 13, respectively, as comprising a compression hole including both ramps 60 and 62, each of the holes 58 included in plates 100 and 110 may alternatively include only one of the ramps 60 and 62 or may comprise a straight-through hole with neither of the ramps 60 and 62.

FIGS. 14–19 illustrate a variety of bone plates which embody the principles of the present invention and have shapes other than the generally rectangular shape of the bone plates illustrated in FIGS. 6–13. Each of the bone plates illustrated in FIGS. 14–19 comprise one-third semi-tubular plates which are typically applied to metaphyseal bone, which is the relatively spongy bone near a joint. In contrast, compression plates are typically attached to cortical bone, which is the relatively hard bone near a joint. Each of the one-third semi-tubular plates illustrated in FIGS. 14–19, have a relatively smaller thickness than compression plates and therefore the included interior holes are straight through holes, and do not include compression ramps. The subsequently discussed bone plates shown in FIGS. 14–16 and 17 are typically used to stabilize a fractured tibia at a location proximate the knee or to stabilize a distal radius. The bone plates shown in FIGS. 18 and 19 are typically used to stabilize a fractured ankle.

FIG. 14 illustrates a bone plate 120 according to a fourth embodiment of the present invention. Plate 120 includes a first end portion 122 and a second end portion 124 longitudinally spaced from end portion 122. An intermediate portion 126 extends between and interconnects the first 122 and second 124 end portions. End portions 122 and 124 and intermediate portion 126 are preferably made as a unitary construction. Bone plate 120 further includes a longitudinally extending axis 128 with end portion 124 and intermediate portion 126 being substantially symmetrically disposed about axis 128. End portion 122 is asymmetrically disposed about axis 128. As shown in FIG. 14, bone plate 120 is generally L-shaped with the end portion 122 extending laterally away from a first side 130 of the intermediate portion 126.

The first 122 and second 124 end portions, and the intermediate portion 126 of bone plate 120 combine to define an upper surface 132, a lower surface 133 and an edge 134 which comprises a perimeter of bone plate 120. Plate 120 further includes a pair of interior holes 136 which extend through plate 120 from the upper surface 132 to the lower surface 133 and are sized to accept conventional fasteners such as bone screws for attaching plate 120 to a bone. Bone plate 120 further includes a pair of apertures 138 formed in the first end portion 122 and extending through plate 120 from the upper surface 132 to the lower surface 133. Each of the apertures 138 have a generally key-hole shape and include a generally circular interior portion 140 and a slot 142 which communicates with the interior portion 140 and extends longitudinally to and through the edge 134. Bone plate 120 further includes an aperture 144 having a generally key-hole shape formed in the second end portion 124. Aperture 144 includes an oblong interior portion 146 and a slot 148 communicating with interior portion 146 and extending transversely to and through the edge 134. The slot 148 is preferably substantially perpendicular to the centerline axis 128. As shown in FIGS. 16, the upper 132 and lower 133 surfaces of bone plate 120 are slightly curved or contoured in a transverse direction to facilitate attachment of bone plate 120 to a bone.

FIG. 17 illustrates a bone plate 150 according to a fifth embodiment of the present invention. Bone plate 150 is substantially the same as bone plate 120, with the following exceptions. The first end portion 122 of bone plate 120 is replaced with a first end portion 152 which extends laterally away from first 130 and second 131 sides of the intermediate portion 126 of plate 150, with plate 150 being substantially symmetrically disposed about a longitudinally extending centerline axis 154. Accordingly, plate 150 has a generally T-shape. The upper portion 152 includes three of the apertures 138 which extend through plate 150 from the upper surface 132 to the lower surface (not shown in FIG. 17) and extend longitudinally to and through the edge 134.

FIG. 18 illustrates a bone plate 160 according to a sixth embodiment of the present invention. Bone plate 160 is the same as bone plate 120 with the following exceptions. The first end portion 122 of bone plate 120 is replaced by a first end portion 162 which has a generally cloverleaf shape and is symmetrically disposed about a longitudinally extending centerline axis 164 of bone plate 160. In addition to the interior holes 136 which are formed in the intermediate portion 126, bone plate 160 also includes a second plurality of interior holes 166, which are formed in the first end portion 162 and extend through plate 160 from the upper surface 132 to the lower surface (not shown in FIG. 18). The interior holes 166 may have a relatively smaller diameter than the interior holes 136. The pair of apertures 138 of bone plate 120 are replaced by a single aperture 168, having a generally U-shape, which extends longitudinally to and through the edge 134 of bone plate 160.

FIG. 19 illustrates a bone plate 170 according to a seventh embodiment of the present invention. As shown in FIG. 19, bone plate 170 has a generally Y-shape which is defined by a first end portion 172, a second end portion 174 and an intermediate portion 176 which extends between and interconnects end portions 172 and 174. As shown in FIG. 19, the intermediate portion 176 is somewhat tapered laterally and bone plate 170 is substantially symmetrically disposed about a longitudinally extending centerline axis 171. The end portions 172 and 174 and intermediate portion 176 combine to define an upper surface 178, a lower surface (not shown) and an edge 180 which comprises a perimeter of plate 170. Similar to bone plates 120, 150, and 160, bone plate 170 includes a pair of interior holes 136 are formed in the intermediate portion 176 of plate 170, with holes 136 extending through plate 176 from the upper surface 178 to the lower surface. Plate 170 further includes a second plurality of interior holes 182 which are formed in the first end portion 172 and extend through plate 170 from the upper surface 178 to the lower surface and are also sized to receive conventional bone screws. An aperture 184 is formed in the first end portion 172 and disposed laterally between the holes 182. Aperture 184 is generally U-shaped and extends longitudinally to and through the edge 180 of plate 170.

Each of the apertures 138, 144, 168 and 184 which were discussed previously in conjunction with one or more of the bone plates 120, 150, 160, and 170, extend to and through the edge of the corresponding bone plate or plates in which they are included, as discussed previously. Therefore, each of the apertures 138, 144, 168 and 184 may be temporarily positioned around an external fixation rod secured to a fractured bone, at a position proximate the bone, by moving the corresponding bone plate relative to the rods as may be further appreciated with reference to the subsequent discussion associated with FIGS. 30–37. After the external fixation rods have been removed, a bone screw may be inserted through each of the foregoing apertures and into one of the same holes used to secure the external fixation rods to the bone.

FIG. 20 is an exploded assembly plan view illustrating a bone plate assembly 200 according to a first embodiment of the present invention. The bone plate assembly 200 includes a bone plate 202 and a pair of washers 204. Plate 202 has a generally rectangular shape and comprises a compression plate, in the illustrative embodiment. Bone plate 202 differs from the previously discussed bone plates of the present invention since it has end portions with reduced thickness relative to the intermediate portion, to accommodate the thickness of washers 204 as subsequently discussed. Bone plate 202 includes a longitudinally extending centerline axis 205, a first end portion 206, a second end portion 208 and an intermediate portion 210 extending between and interconnecting the first 206 and second 208 end portions. End portions 206 and 208, and intermediate portion 210 combine to define an upper surface 212, a lower surface 214, and an edge 216 which comprises a perimeter of bone plate 202.

Bone plate 202 includes a plurality of the interior holes 58, each of which include ramps 60 and 62 which were discussed previously in conjunction with bone plates 40, 100 and 110. Accordingly, each of the holes 58 may accept a bone screw and cause a longitudinal displacement of bone plate 202, relative to a bone, as bone screws are inserted through holes 58. Bone plate 202 further includes an aperture 218 formed in the first end portion 206 and an aperture 220 formed in the second end portion 208. Both of the apertures 218 and 220 extend through plate 202 from the upper surface 212 to the lower surface 214 and extend to and through the edge 216. Therefore, each of the apertures 218 and 220 may be temporarily positioned around an external fixation rod secured to a fractured bone, at a position proximate the bone, by moving the plate 202 relative to the rods as may be further appreciated with reference to the subsequent discussion associated with FIGS. 30–37. After the external fixation rods have been removed, a bone screw may be inserted through each of the apertures 218 and 220 and into onto of the same holes used to secure the external fixation rods to the bone.

Aperture 218 includes a generally rectangular shaped interior portion 222 and a slot 224 communicating with the interior portion 222 and extending longitudinally to and through the edge 216. Aperture 220 includes a generally rectangular shaped interior portion 226 and a slot 228 communicating with the interior portion 226 and extending transversely, in a direction substantially perpendicular to the longitudinally extending centerline axis 205, to and through the edge 216.

Each of the apertures 218 and 220 have a transverse width 230 which is somewhat larger than the widths of the apertures included in the end portions of bone plates 40, 100, and 110 to accommodate greater flexibility with respect to positioning bone plate 202 relative to a pair of external fixation rods, as subsequently discussed. Due to this accommodation, the width 230 is larger than the head of a conventional bone screw. Consequently, without washers 204, a clamp load could not be effectively applied to the end portions 206 and 208 of bone plate 202 in all instances since the head of a conventional bone screw inserted in either aperture 218 or 220 may not contact or grip the end portion 206 or 208, depending upon the position of the screw within either aperture 218 or 220.

Washers 204 include a generally oblong or elliptically shaped aperture 232 extending therethrough. Each aperture 232 has a length 234 and an oblong or elliptically shaped and radiused countersink 236. When bone plate assembly 200 is assembled, both of the washers 204 are disposed in contacting engagement with the upper surface 212 of bone plate 202, with the lengths 234 of the washer apertures 232 extending transversely relative to bone plate 202. The aperture 232 of one of the washers 204 is aligned with the aperture 218 so that a bone screw may pass through aperture 232 of the corresponding washer 204 and aperture 218. The aperture 232 of the other washer 204 is aligned with the aperture 220 of bone plate 202 to similarly accept a bone screw. The countersink 236 of the aperture 232 of each washer 204 is shaped and sized to receive the head of a conventional bone screw, and accordingly a clamp load may be effectively applied to washers 204 and the end portions 206 and 208 of bone plate 202 as bone screws are inserted through each washer 204 and apertures 218 and 220 and into a fractured bone. Furthermore, countersinks 236 permit the top of each bone screw head to be substantially flush with the top surface of the corresponding washer 204 when threaded into the bone.

The first end portion 206 of bone plate 202 has a thickness 238 and end portion 208 has a thickness 240. Preferably, thicknesses 238 and 240 are substantially equal to one another. The intermediate portion 210 of bone plate 202 has a thickness 242 which is greater than thicknesses 238 and 240. The difference in magnitude of thickness 242 as compared to either thickness 238 or thickness 240 is substantially equal to a thickness 244 of washer 204. Accordingly, when washers 204 are disposed on end portions 206 and 208, the top surface of each washer 204 is substantially aligned, or flush with the portion of the upper surface 212 existing in the intermediate portion 210 of bone plate 202. The reduced thickness of end portions 206 and 208 reduces the overall thickness of the bone plate assembly, and therefore reduces the chance of the assembly creating a bulge in the skin overlying the bone to be reduced and stabilized. As shown in FIG. 22, each of the washers 204 is longitudinally curved to match the contour of the upper surface 212 which is shown in FIG. 23.

Figure 24:
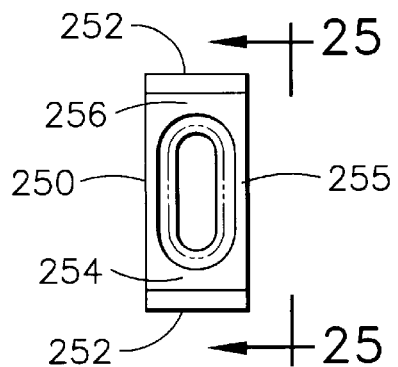
FIG. 24 is a plan view of a washer according to an alternative embodiment of the present invention.
Figure 25:
FIG. 25 is a side elevation view taken along line 25—25 in FIG. 24.

FIGS. 24 and 25 illustrate a washer 250 according to an alternative embodiment of the present invention. Bone plate assembly 200 may include a pair of washers 250 in lieu of washers 204. Washers 250 may be the same as washers 204 except that washers 250 include means for laterally retaining the washers 250 on bone plate 202 which comprises a pair of tabs, or flanges 252. One of the tabs 252 is attached to a first end 254 of a remaining portion 255 of washer 250, while the other tab 252 is attached to an opposite end 256 of the remaining portion 255 of washer 250. Flanges or tabs 252 may be substantially perpendicular to the ends 254 and 256 of the remaining portion 255 of washer 250. Flanges 252 allow each of the washers 250 to be slid in a longitudinal direction along bone plate 202, but prevent washers 250 from disengaging bone plate 202 in a lateral direction. Flanges 252 may be attached to the remaining portion 255 of washer 250 or alternatively, may be integrally formed with portion 255 as a unitary construction. When washers 250 are positioned on the bone plate 202, each of the flanges 252 extends downward toward the lower surface 214 of plate 202 and is positioned adjacent the edge 216 of plate 202.

Figure 26:
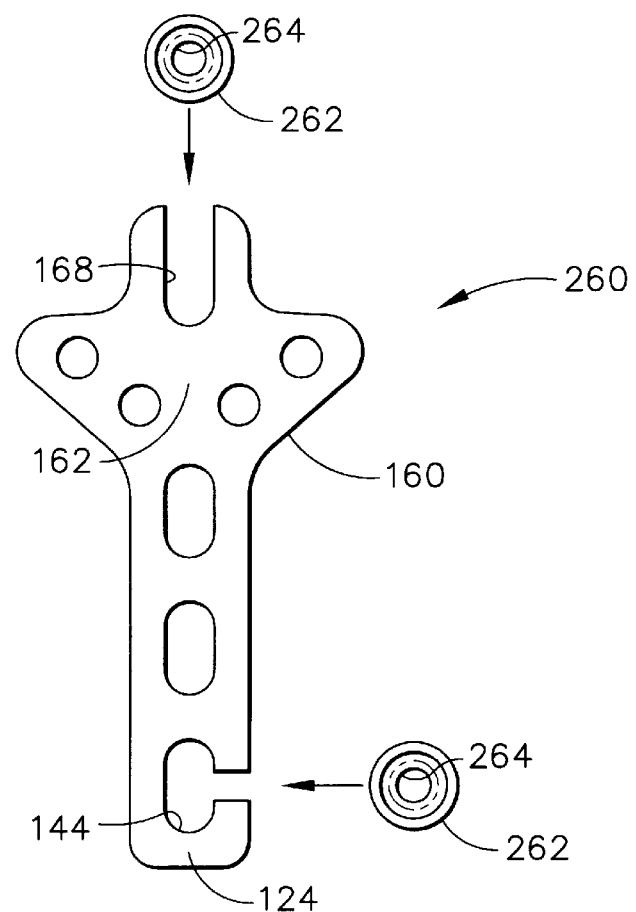
FIG. 26 is an exploded assembly plan view illustrating a bone plate assembly according to a second embodiment of the present invention.

FIG. 26 illustrates a bone plate assembly 260 according to a second embodiment of the present invention. Bone plate assembly 260 includes the bone plate 160, discussed previously and a pair of washers 262, each having an aperture or hole 264 extending therethrough. Aperture 264 includes a radiused countersink which is shaped and sized to receive the head of a conventional bone screw. The hole 264 of one of the washers 262 is aligned with the aperture 168 formed in bone plate 160, to accept a conventional bone screw, while the hole 264 of the other washer 262 is aligned with aperture 144 in bone plate 160 to accept another conventional bone screw. The bone plate assembly 260 may be advantageously used to more evenly distribute the clamp load applied by the bone screws to the end portions 162 and 124 of bone plate 160, when apertures 168 and 144 are sized to permit the head of a conventional bone screw to apply a clamp load to end portions 162 and 124. However, bone plate assembly 260 is particularly useful when apertures 144 and 168 are larger than the head of a conventional bone screw, such that the bone screw could otherwise pass through apertures 144 and 168 without applying a clamp load to the end portions 124 and 162 of plate 160.

FIGS. 27–29 illustrate a bone plate assembly 270 according to a third embodiment of the present invention. Assembly 270 includes a bone plate 272 and a pair of the washers 204. Bone plate 272 includes a first end portion 276, a second end portion 278 and an intermediate portion 280 extending between and interconnecting the first 276 and second 278 end portions. As shown in FIG. 27, each of the end portions 276 and 278 as well as the intermediate portion 280 have a generally rectangular shape. However, bone plate 272 differs from the previously described bone plates of the present invention having a generally rectangular shape, since the end portions 276 and 278 are enlarged laterally relative to the intermediate portion 280, as subsequently discussed. End portions 276 and 278 and intermediate portion 280 combine to define an upper surface 282, a lower surface 284 and an edge 286 which comprises a perimeter of bone plate 272. Bone plate 272 further includes a plurality of interior holes 58, with each of the holes 58 including ramps 60 and 62 which were discussed previously. Accordingly, each of the holes 58 may accept a bone screw and may cause a longitudinal displacement of bone plate 272, relative to a bone (not shown), as bone screws are inserted through holes 58.

Bone plate 272 further includes an aperture 288 formed in the first end portion 276 and an aperture 290 formed in the second end portion 278. Both of the apertures 288 and 290 extend through plate 272 from the upper surface 282 to the lower surface 284 and extend to and through the edge 286. Therefore, each of the apertures 288 and 290 may be temporarily positioned around an external fixation rod secured to a fractured bone, at a position proximate the bone, by moving the plate 272 relative to the rods as may be further appreciated with reference to the subsequent discussion associated with FIGS. 30–37. After the external fixation rods have been removed, a bone screw may be inserted through each of the apertures 288 and 290 and into one of the same holes used to secure the external fixation rods to the bone.

Aperture 288 includes an interior portion 292 having a generally rectangular shape in the illustrative embodiment, and a slot 294 communicating with interior portion 292 and extending transversely to and through the edge 286. Aperture 290 includes an interior portion 296, having a generally rectangular shape in the illustrative embodiment, and a slot 298 which communicates with the interior portion 296 and extends longitudinally to and through the edge 286 of plate 272.

End portion 276 has a width 300, end portion 278 has a width 302, and intermediate portion 280 has a width 304. Widths 300 and 302 are preferably substantially equal to one another and are greater than width 304. The enlarged widths 300 and 302 of end portions 276 and 278 respectively, permit apertures 288 and 290 to have an increased size relative to the previously discussed bone plates, which may facilitate placement of the bone plate relative to external fixation rods, as subsequently discussed. For instance, the interior portion 292 of aperture 288 has a width 306 and the interior portion 296 of aperture 290 has a width 308 which is preferably substantially the same as width 306. Widths 306 and 308 may be substantially the same as width 304 of the intermediate portion 280 of bone plate 272 or may even be somewhat larger to accommodate greater flexibility with respect to positioning bone plate 272 relative to a pair of external fixation rods, as subsequently discussed. The end portions 276 and 278, and intermediate portion 280, are substantially symmetrically disposed about a longitudinally extending centerline axis 299 of bone plate 272.

FIG. 27 is an exploded assembly plan view of bone plate assembly 270 with the washers 204 separated from bone plate 272 for purposes of illustration. However, when bone plate assembly 270 is assembled, both of the washers 204 are disposed in contacting engagement with the upper surface 282 of bone plate 272. The long sides of washers 204 are sized so that they may span across one of the end portions 276 and 278 of bone plate 272. When assembled, the aperture 232 of one of the washers 204 is aligned with the aperture 288 formed in end portion 276 of bone plate 272, so that a bone screw may pass through aperture 232 and aperture 288. The aperture 232 of the other washer 204 is aligned with the aperture 290 formed in the end portion 278 of bone plate 272. Alternatively, bone plate assembly 270 may incorporate a pair of the washers 250 in lieu of the washers 204, with the washers 250 being sized to span across one of the end portions 276 and 278.

End portions 276 and 278 have thicknesses 310 and 312, respectively, which are preferably substantially equal to one another. The intermediate portion 280 of bone plate 272 has a thickness 314 which is greater than the thicknesses 310 and 312. The difference between the thickness 314 and either thickness 310 or thickness 312 is substantially equal to the thickness of washer 204 for the reasons discussed previously with respect to bone plate assembly 200. As shown in FIG. 29, bone plate 272 is slightly curved, or contoured in a transverse direction to facilitate attaching bone plate 272 to a bone, similar to the previously discussed bone plates of the present invention.

A wide variety of additional bone plate assemblies are considered to be within the scope of the present invention. For instance, while the apertures in the end portions 206 and 208 of bone plate 202 are configured similar to the apertures 76 and 78 of bone plate 40 (i.e., with one of the apertures 218 and 220 extending longitudinally to and through edge 216 and the other extending transversely to and through edge 216), bone plate 202 may include a pair of apertures in lieu of apertures 218 and 220 which are configured as shown with respect to the apertures included in bone plates 100 or 110. Furthermore, apertures 218 and 220 may have other shapes such as key-hole or generally U-shapes, provided that each of the apertures formed in end portions 206 and 208 extend to and through the edge 216 of bone plate 210. Additionally, bone plate assemblies according to the present invention may comprise bone plates configured as shown with respect to bone plates 40, 100 and 110, without reduced end portion thicknesses, in combination with a pair of washers 204 or a pair of washers 250 if the bone plates comprise one-third semi-tubular plates having reduced thickness relative to compression plates, so that the overall thickness of the bone plate assembly is not excessive. Furthermore, bone plate assemblies according to the present invention may include one of the bone plates 120, 150 and 170 discussed previously, in combination with a pair of washers such as washers 262. Also, bone plate assemblies embodying the principles of the present invention may include bone plates having shapes other than those shown in the illustrated embodiments, provided the plate includes an aperture formed in each end which extends to and through the edge of the plate, and may include washers having shapes other than those shown with respect to washers 204 and 250, provided the washers are sized and shaped consistently with the shape of the particular plate and included end portion apertures.

Figure 30:
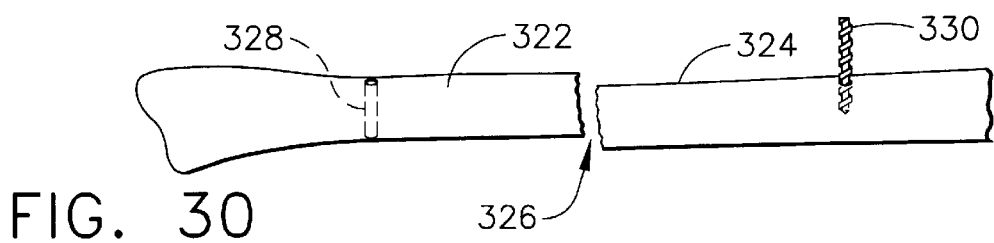
FIG. 30 is a fragmentary side elevation view illustrating the step of drilling holes through a bone to accept an external fixator.

The method of attaching the bone plates and bone plate assemblies of the present invention to a reduced, fractured bone may be further understood with reference to FIGS. 30–37. Although several steps of the method of the present invention are illustrated with respect to the bone plate assembly 200 and the included generally rectangular plate 202, the method is substantially the same regardless of the particular bone plate or bone plate assembly being used. Also, the incorporation of washers only pertains to the various bone plate assemblies, with the method being otherwise the same for the application of a bone plate or a bone plate assembly. In each case, the bone plate may be advantageously used in combination with a pair of external fixation rods 320, shown in FIG. 31, to avoid the problems associated with the use of conventional bone plates discussed previously. FIG. 30 is a fragmentary view showing a portion of a fractured radius having a first portion 322 and a second portion 324 separated by a fracture indicated generally at 326. FIG. 30 illustrates a hole 328 drilled through the portion 322 of the fractured radius and shows a drill bit 330 in the process of drilling a hole through the portion 324 of the fractured radius.

Figure 31:
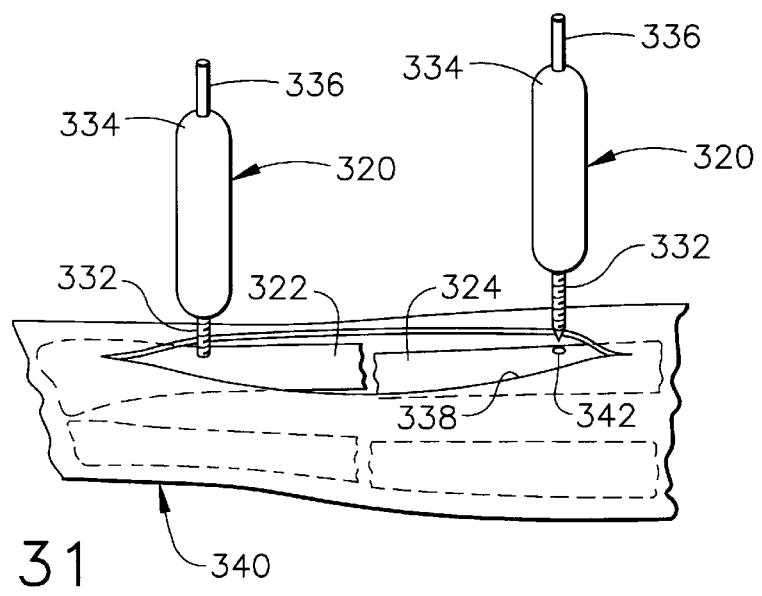
FIG. 31 is a perspective view illustrating the step of inserting external fixators into an incision in a fractured right arm of a human and into the drilled holes shown in FIG. 30.
Figure 32:
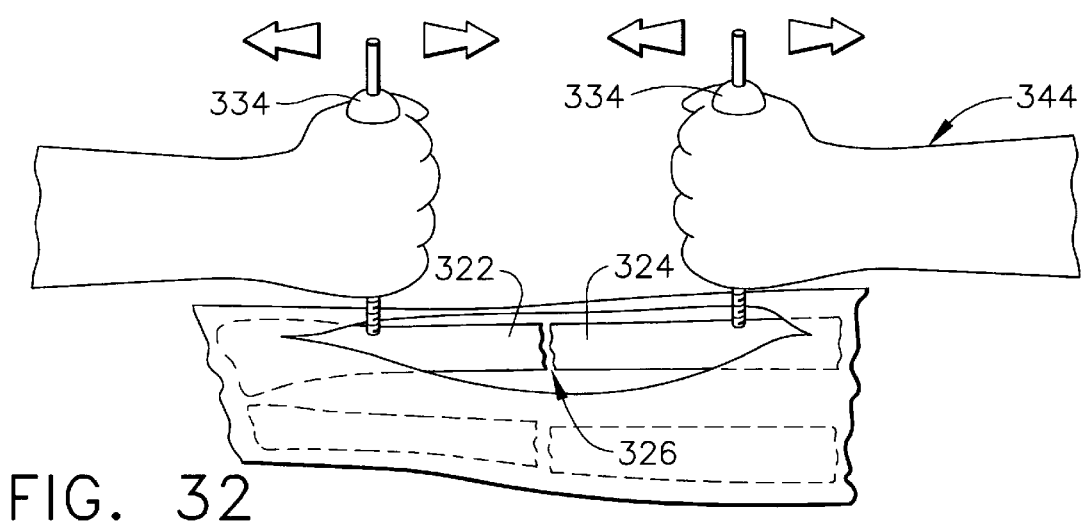
FIG. 32 is a perspective view illustrating the step of reducing the fractured radius shown in FIG. 31.

As shown in FIG. 31, each of the external fixation rods 320 has a lower threaded portion 332, a handle portion 334, and an upper portion 336. As shown in FIG. 31, the lower threaded portion 332 of one of the external fixation rods 320 is inserted through an incision 338 in the right arm 340 of a person, and into the hole 328 drilled into portion 322 of the fractured radius. The other external fixation rod 320 is in the process of being inserted into a hole 342 drilled into the portion 324 of the fractured radius. The holes 328 and 342 are preferably drilled substantially perpendicularly at least partially through the portions 322 and 324, respectively, of the fractured radius at approximately equal distances from the fracture site 326 and/or in the area best suited for placement of the bone plate 202. After the external fixation rods 320 have been inserted in the fractured portions 322 and 324 of the radius, an orthopedic surgeon 344 may grasp the handle portions 334 of the external fixation rods 320, as shown in FIG. 32 and move the portions 322 and 324 of the fractured radius as required to reduce the fracture 326.

Figure 33:
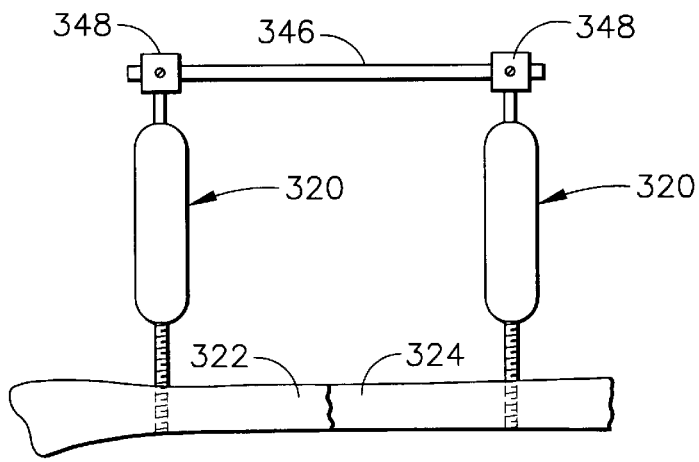
FIG. 33 is an elevation view illustrating the step of securing a pair of external fixators after the fractured radius has been reduced.

Once the fracture 326 has been reduced, so that portions 322 and 324 of the fractured radius are substantially in abutting relationship with one another, as shown in FIG. 33, an external fixation frame 346 is attached to the upper ends 336 of the external fixation rods 320 and is secured by a pair of clamp assemblies 348, so as to secure portions 322 and 324 of the fractured radius in an aligned relationship. The surgeon 344 may then assess the fracture alignment and re-manipulate as required.

Figure 34:
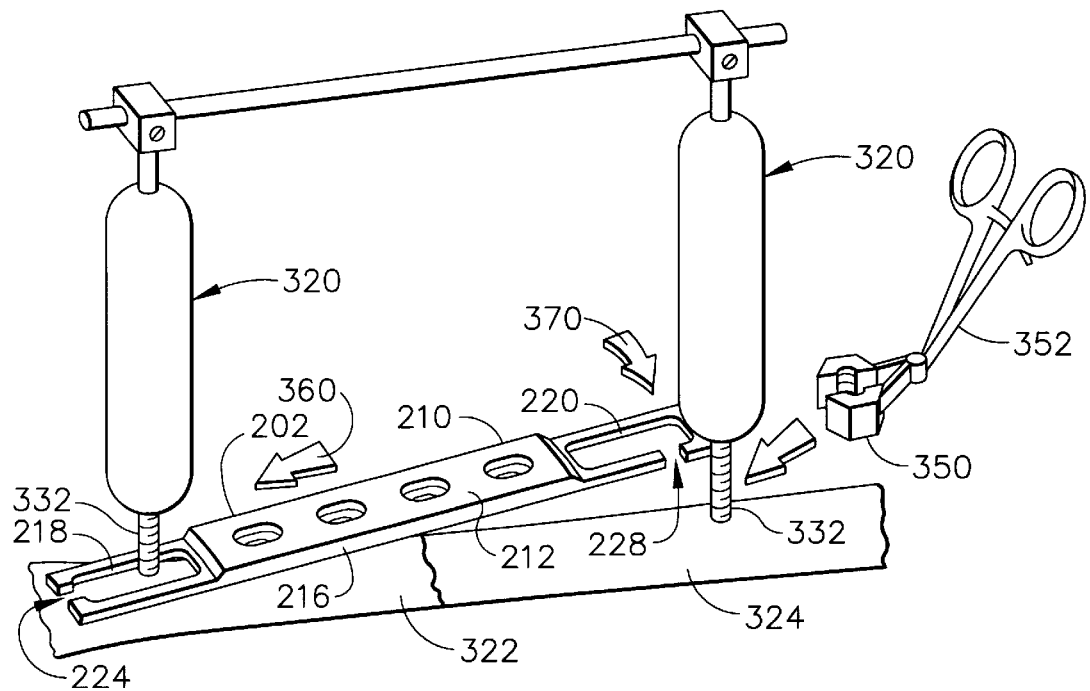
FIG. 34 is a perspective view illustrating the step of installing a bone plate according to the present invention.

Once the surgeon 344 is satisfied with the fracture alignment, the bone plate 202 of bone plate assembly 200 may be positioned. As shown in FIG. 34, the plate 202 may be moved transversely relative to the external fixation rod 320 which is secured to the portion 322 of the fractured radius, as indicated generally by the direction arrow 360, so that the aperture 218 as positioned around the lower threaded portion 332 of the rod 320 secured to portion 322 at a position proximate the portion 322. Next, the plate 202 is moved transversely relative to the external fixation rod 320 secured to the portion 324 of the fractured radius, as indicated generally by direction arrow 370, so that the aperture 220 is positioned around the lower threaded portion 332 of the rod 320 secured to portion 324 at a position proximate portion 324. The bone plate 202 may optionally be temporarily held in place by a pair (one shown) of bifurcated washers 350, with each washer 350 being attached to a clamp 352 and positioned around the lower threaded portion 332 of one of the external fixation rods 320, above the plate 202.

It may be appreciated that the spacing between the holes 328 and 342 to accept the external fixation rods 320 may vary somewhat from the desired spacing. Accordingly, it may be appreciated that increased sizes of the apertures in the end portions of the bone plate to be applied facilitates placement of the bone plate. It may be further appreciated that if both of the apertures in the end portions of the bone plate extend transversely to and through the edge of the plate, such as aperture 78 and 102 of bone plate 100, the placement of the holes to accept the external fixation rods must be somewhat more closely controlled. Also, if a plate such as plate 110 is used, with both of the apertures formed in the end portions extending longitudinally to and through the edge of the bone plate, the angle which the bone plate must be tilted during placement (as shown in FIG. 34), may need to be increased. This may require external fixation rods having handle portions, such as portions 334, to be displaced further away from the bone or removable from the lower threaded portions of the rods. Accordingly, although each of the bone plates and bone plate assemblies illustrated and discussed herein may be advantageously utilized to overcome the problems associated with known bone plates, the embodiments of the present invention incorporating an aperture formed in one end which extends longitudinally to and through the edge of the bone plate and an aperture in the opposite end portion which extends transversely to and through the edge of the bone plate, are the most preferred.

Figure 35:
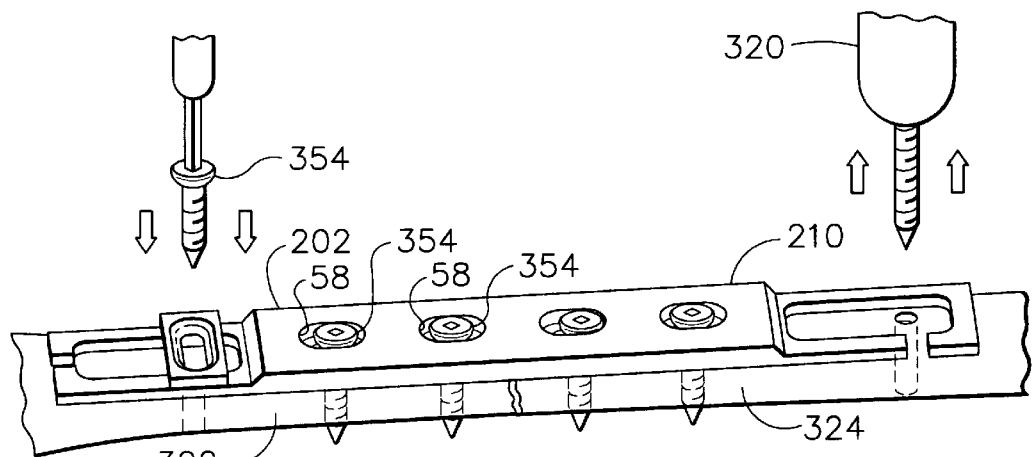
FIG. 35 is a perspective view illustrating the step of securing a bone plate assembly according to the present invention to the fractured and reduced radius.
Figure 36:
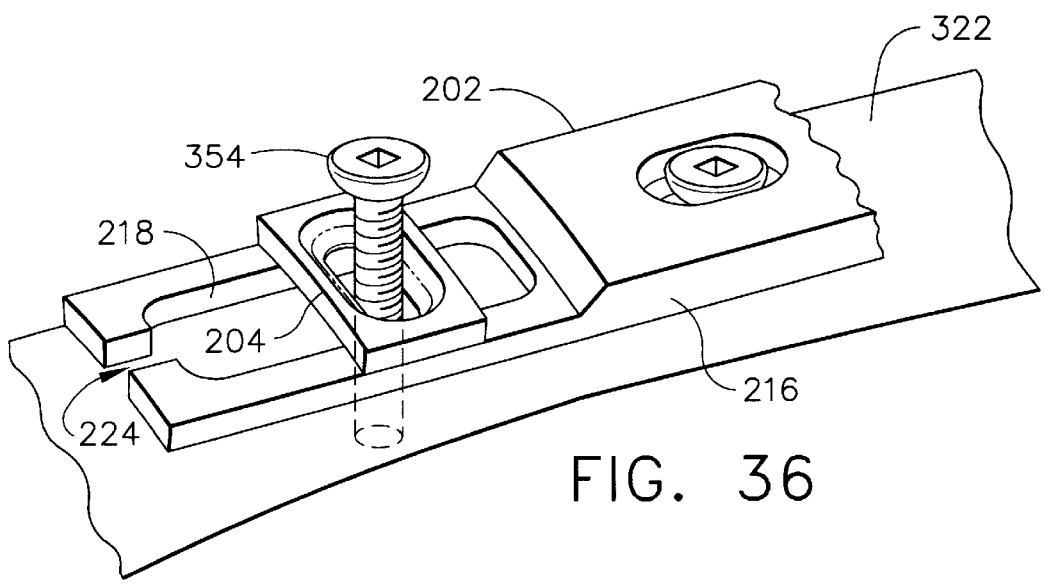
FIG. 36 is a fragmentary, enlarged perspective view further illustrating a portion of the bone plate assembly shown in FIG. 35.
Figure 37:
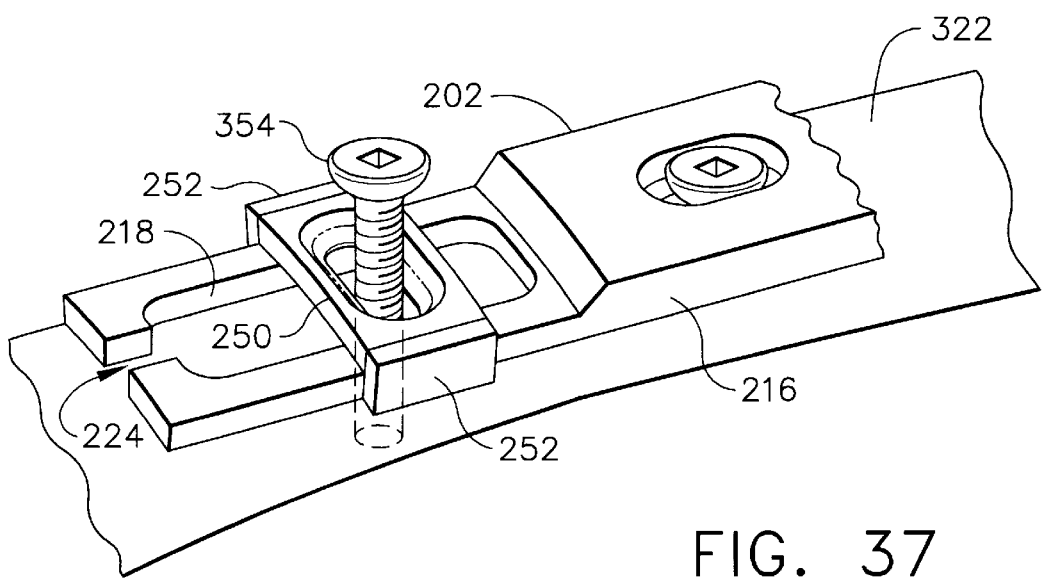
FIG. 37 is a fragmentary, enlarged perspective view similar to that shown in FIG. 36 illustrating a washer according to an alternative embodiment of the present invention.

After the bone plate has been positioned around the pair of external fixation rods, a bone screw 354 is inserted through each of the interior holes 58 of bone plate 202 and threaded into the corresponding one of portions 322 and 324 of the fractured radius to secure the plate 202 to the radius. Each of the external fixation rods 320 is then removed, as shown in FIG. 35 with respect to the rod 320 being removed from portion 324 of the fractured radius. After removal of the corresponding external fixation rod 320, a bone screw 354 is inserted through one of the washers 204 and the aperture 218 and is threaded into the hole 328 in the end portion 322 of the fractured radius as illustrated in FIGS. 35 and 36. Similarly, another bone screw 354 is inserted through the other washer 204 and the aperture 220 and is threaded into the hole 342 in the portion 324 of the fractured radius, to further secure the bone plate 202 to the radius. The holes 328 and 342 are preferably drilled substantially perpendicularly through the portions 322 and 324, respectively, of the fractured radius at approximately equal distances from the fracture site 326 and/or in the area best suited for placement of the bone plate 202 to the radius. Alternatively, washers 250 may be used in lieu of washers 204 as shown in FIG. 37 with respect to aperture 218 in the end portion 206 of bone plate 202. After the bone plate assembly 200 has been secured, x-rays are performed as indicated and the wound is closed in a conventional fashion.

The use of the bone plates and bone plate assemblies of the present invention avoids the problems associated with the attachment of conventional bone plates to a fractured bone and accordingly reduces operating room time, open wound time, anesthesia time and minimizes the risk to the patient.

While the foregoing description has set forth the preferred embodiments of the present invention in particular detail, it must be understood that numerous modifications, substitutions and changes can be undertaken without departing from the true spirit and scope of the present invention as defined by the ensuing claims. The invention is therefore not limited to specific preferred embodiments as described, but is only limited as defined by the following claims.

What is claimed is:

1. A bone plate for use in stabilizing a bone having a fracture site, the bone being reduced by a pair of external fixation rods secured to the bone on either side of the fracture site, said bone plate comprising:

a longitudinally extending axis;

first and second end portions longitudinally spaced from one another;

an intermediate portion extending between and interconnecting said first and second end portions, said first and second end portions and said intermediate portion combining to define an upper surface, a lower surface for application to the bone, and an edge extending between said upper surface and said lower surface, said edge comprising a perimeter of said bone plate;

at least one interior hole formed in said intermediate portion for receiving a bone screw, said at least one interior hole extending through said plate from said upper surface to said lower surface, said at least one interior hole being spaced apart from said edge; and a plurality of apertures formed in said plate, each said aperture extending through said plate from said upper surface to said lower surface, each said aperture extending to and through said edge whereby said aperture may be temporarily positioned around one of the external fixation rods, at a position proximate the bone, by moving said plate relative to said rod, said aperture being effective for receiving a bone screw after the rod is removed from the bone; wherein said first end portion includes at least one of said apertures;

said second end portion includes at least one of said apertures;

at least one of said apertures formed in said plate extends transversely to said axis, to and through said edge.

2. The bone plate as recited in claim 1, wherein:

said first and second end portions each include a single one of said apertures;

said single aperture formed in said first end portion extends longitudinally to said axis, to and through said edge;

said single aperture formed in said second end portion extends transversely to said axis, to and through said edge.

3. The bone plate as recited in claim 2, wherein:

said plate has a generally rectangular shape.

4. The bone plate as recited in claim 3, wherein:

each of said apertures includes an interior portion and a slot, said slot communicating with said interior portion and extending to and through said edge.

5. The bone plate as recited in claim 4, wherein:
said interior portion of each of said apertures has a generally rectangular shape.
6. The bone plate as recited in claim 2, wherein:
said first end portion of said plate has a generally cloverleaf shape;
said intermediate portion and said second end portion have a generally rectangular shape.
7. The bone plate as recited in claim 6, wherein:
said at least one interior hole comprises a plurality of said interior holes formed in said intermediate portion, wherein each of said first plurality of interior holes extends through said plate from said upper surface to said lower surface and is spaced apart from said edge;
said bone plate further comprises a second plurality of interior holes formed in said first end portion for receiving a plurality of bone screws, said second plurality of interior holes extending through said plate from said upper surface to said lower surface, each of said second plurality of interior holes being spaced apart from said edge.
8. The bone plate as recited in claim 2, wherein:
said plate is generally Y-shaped.
9. The bone plate as recited in claim 8, wherein:
said at least one interior hole comprises a plurality of said interior holes formed in said intermediate portion, wherein each of said first plurality of interior holes extends through said plate from said upper surface to said lower surface and is spaced apart from said edge;
said bone plate further comprises a second plurality of interior holes formed in said first end portion for receiving a plurality of bone screws, said second plurality of interior holes extending through said plate from said upper surface to said lower surface, said second plurality of interior holes being spaced apart from said edge.
10. The bone plate as recited in claim 9, wherein:
said second plurality of interior holes comprises a pair of interior holes;
said aperture formed in said first end portion is disposed laterally between said pair of interior holes.
11. The bone plate as recited in claim 1, wherein:
said first and second end portions each include a single one of said apertures;
said single aperture formed in said first end extends transversely to said axis, to and through said edge;
said single aperture formed in said second end portion extends transversely to said axis, to and through said edge.
12. The bone plate as recited in claim 11, wherein:
said plate has a generally rectangular shape.
13. The bone plate as recited in claim 12, wherein:
each of said apertures includes an interior portion and a slot, said slot communicating with said interior portion and extending to and through said edge.
14. The bone plate as recited in claim 13, wherein:
said interior portion of each of said apertures has a generally rectangular shape.
15. The bone plate as recited in claim 1, wherein:
said first end portion includes at least two of said apertures, each extending longitudinally to said axis, to and through said edge;
said second end portion includes a single one of said apertures extending transversely to said axis, to and through said edge.

16. The bone plate as recited in claim 15, wherein:
said plate is generally L-shaped.
17. The bone plate as recited in claim 16, wherein:
said first end portion includes two of said apertures;
said first end portion extends laterally away from a first side of said intermediate portion.
18. The bone plate as recited in claim 15, wherein:
said plate is generally T-shaped.
19. The bone plate as recited in claim 18, wherein:
said first end portion includes three of said apertures;
said first end portion extends laterally away from first and second sides of said intermediate portion.
20. The bone plate as recited in claim 1, wherein:
said at least one interior hole comprises a plurality of said interior holes formed in said intermediate portion, wherein each of said interior holes extends through said plate from said upper surface to said lower surface and is spaced apart from said edge;
at least one of said interior holes comprises a compression hole having at least one contoured ramp extending between said upper surface and said lower surface, said compression hole permitting displacement of said bone plate in a longitudinal direction as a bone screw is inserted into said compression hole;
said bone plate is a compression bone plate.
21. The bone plate as recited in claim 20, wherein:
each of said interior holes comprises a compression hole having at least one of said contoured ramps extending between said upper surface and said lower surface, thereby permitting displacement of said bone plate in a longitudinal direction as bone screws are inserted through said compression holes.
22. The bone plate as recited in claim 20, wherein:
each of said interior holes includes a pair of said contoured ramps extending between said upper surface and said lower surface thereby permitting displacement of said bone plate in one of first and second longitudinal directions as bone screws are inserted through said compression holes.
23. The bone plate as recited in claim 1, wherein:
said at least one interior hole comprises a plurality of said interior holes formed in said intermediate portion, wherein each of said interior holes extends through said plate from said upper surface to said lower surface and is spaced apart from said edge;
each of said interior holes comprises a straight-through hole;
said bone plate is a one-third semi-tubular bone plate.
24. The bone plate as recited in claim 1, wherein:
said bone plate is made of metal.
25. The bone plate as recited in claim 1, wherein:
said first and second end portions and said intermediate portion are made as a unitary construction.
26. The bone plate as recited in claim 1, wherein:
said longitudinally extending axis comprises a longitudinally extending centerline axis.
27. The bone plate as recited in claim 26, wherein:
said bone plate is substantially symmetrically disposed laterally about said centerline axis.
28. The bone plate as recited in claim 27, wherein:
said at least one interior hole comprises a plurality of said interior holes formed in said intermediate portion, wherein each of said interior holes extends through said plate from said upper surface to said lower surface and is spaced apart from said edge;

said interior holes are disposed along said centerline axis.

29. The bone plate is recited in claim 1, wherein:

said lower surface is contoured to facilitate application of said bone plate to the bone.

30. A bone plate assembly for use in stabilizing a fractured bone, said bone plate assembly comprising:

a bone plate; and a pair of washers, each of said washers including an interior aperture and being in contacting engagement with said bone plate;

wherein said bone plate comprises:

first and second end portions longitudinally spaced from one another;

an intermediate portion extending between and interconnecting said first and second end portions, said first and second end portions and said intermediate portion combining to define an upper surface, a lower surface for application to the bone, and an edge extending between said upper surface and said lower surface, said edge comprising a perimeter of said bone plate;

at least one interior hole formed in said intermediate portion for receiving a plurality of bone screws to secure said plate to the bone, said interior holes extending through said plate from said upper surface to said lower surface, said interior holes being spaced apart from said edge; and a plurality of apertures formed in said plate, each said aperture extending through said plate from said upper surface to said lower surface for receiving a bone screw, each said aperture extending to and through said edge, each of said first and second end portions including at least one of said apertures;

wherein each of said washers is disposed in contacting engagement with said upper surface of said bone plate;

wherein said interior aperture of one of said washers is aligned with a first one of said apertures and said interior aperture of the other of said washers is aligned with a second one of said apertures, said first and second apertures being formed in said first end portion and said second end portion, respectively.

31. The bone plate assembly as recited in claim 30, wherein:

said first and second end portions of said bone plate each include a single one of said apertures;

said single aperture formed in said first end portion extends longitudinally to and through said edge;

said single aperture formed in said second end portion extends transversely to and through said edge.

32. The bone plate assembly as recited in claim 30, wherein:

said first and second end portions each include a single one of said apertures;

said single aperture formed in said first end portion extends transversely to and through said edge;

said single aperture formed in said second end portion extends transversely to and through said edge.

33. The bone plate assembly as recited in claim 30, wherein:

said first and second end portions each include a single one of said apertures;

each of said apertures extends longitudinally to and through said edge.

34. The bone plate assembly as recited in claim 30, wherein:

said first end portion includes as least two of said apertures, each extending longitudinally to and through said edge;

said second end portion includes a single one of said apertures extending transversely to and through said edge.

35. The bone plate assembly as recited in claim 30, wherein:

said bone plate and each of said washers have a generally rectangular shape.

36. The bone plate assembly as recited in claim 35, further comprising:

means for laterally retaining said washers on said bone plate.

37. The bone plate assembly as recited in claim 36, wherein:

said means for laterally retaining said washers comprises a pair of tabs attached to each of said washers, each of said tabs being attached to one end of the corresponding one of said washers.

38. The bone plate assembly as recited in claim 35, wherein:

each of said apertures formed in said plate includes an interior portion and a slot, said slot communicating with said interior portion and extending to and through said edge of said plate.

39. The bone plate assembly as recited in claim 38, wherein:

said interior portion of each of said apertures formed in said bone plate has a generally rectangular shape.

40. The bone plate assembly as recited in claim 30, wherein:

said first and second end portions have a first thickness;

said intermediate portion has a second thickness which is greater than said first thickness.

41. The bone plate assembly as recited in claim 30, wherein:

each of said washers has a generally round shape.

42. The bone plate assembly as recited in claim 30, wherein:

said first end portion has a first width, said second end portion has a second width, and said intermediate portion has a third width;

said first and second widths are greater than said third width.

43. The bone plate assembly as recited in claim 42, wherein:

said apertures include an interior portion having a fourth width;

said fourth width is substantially the same as said third width.

* * * * *